United States Patent
Freeman et al.

(10) Patent No.: US 11,628,038 B2
(45) Date of Patent: Apr. 18, 2023

(54) MULTI-OPTION ALL-DIGITAL 3D SURGERY VISUALIZATION SYSTEM AND CONTROL

(71) Applicant: Raytrx, LLC, Tulsa, OK (US)

(72) Inventors: Michael Hayes Freeman, Tulsa, OK (US); Mitchael C. Freeman, Sapulpa, OK (US); Jordan Boss, Tulsa, OK (US); Brian Santee, Tulsa, OK (US); Montgomery H. F. Freeman, Dana Point, CA (US); Thomas A. Finley, Tulsa, OK (US); Linda Lam, Sierra Madre, CA (US); Victoria McArtor, Tulsa, OK (US); Steven Yeager, Colorado Springs, CO (US); David Kessler, Rochester, NY (US); Ian Oswald, Stillwater, OK (US)

(73) Assignee: Raytrx, LLC, Tulsa, OK (US)

( * ) Notice: Subject to any disclaimer, the term of this patent is extended or adjusted under 35 U.S.C. 154(b) by 133 days.

(21) Appl. No.: 17/182,022

(22) Filed: Feb. 22, 2021

(65) Prior Publication Data
US 2021/0315662 A1 Oct. 14, 2021

Related U.S. Application Data

(60) Provisional application No. 63/019,796, filed on May 4, 2020, provisional application No. 63/005,202, filed
(Continued)

(51) Int. Cl.
*A61B 90/00* (2016.01)
*G02B 27/01* (2006.01)
*G06F 3/01* (2006.01)

(52) U.S. Cl.
CPC .............. *A61B 90/37* (2016.02); *A61B 90/39* (2016.02); *G02B 27/0172* (2013.01);
(Continued)

(58) Field of Classification Search
CPC ... A61B 90/37; A61B 90/39; A61B 2090/365; G02B 27/0172; G06F 3/012; G06F 3/013
(Continued)

(56) References Cited

U.S. PATENT DOCUMENTS 7,639,208 B1   12/2009   Ha et al.
8,135,227 B2   3/2012   Lewis et al.
(Continued)

FOREIGN PATENT DOCUMENTS

JP   09245195   9/1997
KR   10-2014-0112207   9/2014
KR   1020180068351   6/2018

OTHER PUBLICATIONS

KIPO, "International Search Report", dated Jun. 16, 2016, Published in: WO.
(Continued)

*Primary Examiner* — Mark Edwards
(74) *Attorney, Agent, or Firm* — Head, Johnson, Kachigian & Wilkinson, PC

(57) ABSTRACT

An augmented reality and extended reality surgical system comprising three 3D viewing options of: (i) an AR/XR headset or headsets, (ii) one or more autostereoscopic "3D glasses free" monitor(s); and (iii) one or more digital ocular stereoscopic 3D viewports which is mounted to a cobotic arm viewing option for ergonomically sound viewing. The system may comprise a wearable device, such as a head mounted display or glasses, that provides the user with virtual reality, augmented reality, and/or mixed reality for surgery visualization. This system is all digital and features both wired and wireless connections that have approximately the same latency of less than 20 milliseconds. This may allow the user to access 2D or 3D imaging, magnification, virtual visualization, six-degrees of freedom (6DoF) image management, and/or other images while still viewing
(Continued)

real reality and thus maintaining a presence in the operating room. The all-digital multi-option 3D viewing surgery system provides an ergonomically sound surgery visualization system.

13 Claims, 17 Drawing Sheets

Related U.S. Application Data on Apr. 3, 2020, provisional application No. 62/986,461, filed on Mar. 6, 2020, provisional application No. 62/979,999, filed on Feb. 21, 2020.

(52) U.S. Cl.
CPC .............. *G06F 3/012* (2013.01); *G06F 3/013* (2013.01); *A61B 2090/365* (2016.02)

(58) Field of Classification Search
USPC ........................................................ 606/130
See application file for complete search history.

(56) References Cited

U.S. PATENT DOCUMENTS

| | | | |
|---|---|---|---|
| 8,311,328 B2 | 11/2012 | Spruck | |
| 8,350,898 B2 | 1/2013 | Chang et al. | |
| 8,494,298 B2 | 7/2013 | Lewis et al. | |
| 8,771,805 B2 | 7/2014 | Laude et al. | |
| 8,798,756 B2 | 8/2014 | McClure et al. | |
| 8,812,120 B2 | 8/2014 | Greenberg et al. | |
| 8,831,734 B2 | 9/2014 | Nanduri et al. | |
| 8,831,745 B2 | 9/2014 | Hung et al. | |
| 8,874,224 B2 | 10/2014 | Greenberg et al. | |
| 8,874,239 B2 | 10/2014 | Greenberg et al. | |
| 8,886,329 B2 | 11/2014 | Greenberg et al. | |
| 8,912,979 B1 | 12/2014 | Gomez | |
| 8,934,983 B2 | 1/2015 | Greenberg et al. | |
| 8,954,157 B2 | 2/2015 | Faraji et al. | |
| 8,976,086 B2 | 3/2015 | Hilkes | |
| 9,002,462 B2 | 4/2015 | McClure et al. | |
| 9,042,985 B2 | 5/2015 | Marsh et al. | |
| 9,044,590 B2 | 6/2015 | Greenberg et al. | |
| 9,044,591 B2 | 6/2015 | Greenberg et al. | |
| 9,050,468 B2 | 6/2015 | Greenberg et al. | |
| 9,061,150 B2 | 6/2015 | Greenberg et al. | |
| 9,072,888 B2 | 7/2015 | Greenberg et al. | |
| 9,072,900 B2 | 7/2015 | Caspi et al. | |
| 9,078,739 B2 | 7/2015 | Greenberg et al. | |
| 9,084,895 B2 | 7/2015 | Greenberg et al. | |
| 9,089,690 B2 | 7/2015 | Greenberg et al. | |
| 9,089,701 B2 | 7/2015 | Zhou et al. | |
| 9,089,702 B2 | 7/2015 | Dorn et al. | |
| 9,095,709 B2 | 8/2015 | McClure et al. | |
| 9,095,710 B2 | 8/2015 | Horsager et al. | |
| 9,095,722 B2 | 8/2015 | Meeh et al. | |
| 9,097,891 B2 | 8/2015 | Border et al. | |
| 9,651,784 B2 | 5/2017 | Osterhout | |
| 9,955,862 B2 | 5/2018 | Freeman et al. | |
| 10,111,583 B1 | 10/2018 | Freeman et al. | |
| 10,149,958 B1 | 12/2018 | Tran et al. | |
| 10,345,768 B2 | 7/2019 | Fullam et al. | |
| 10,638,080 B2 | 4/2020 | Ovchinnikov et al. | |
| 10,874,297 B1 | 12/2020 | Freeman et al. | |
| 2002/0082498 A1 | 6/2002 | Wendt et al. | |
| 2005/0168569 A1 | 8/2005 | Igarashi et al. | |
| 2005/0280603 A1 | 12/2005 | Aughey et al. | |
| 2007/0121070 A1 | 5/2007 | Alster et al. | |
| 2009/0123036 A1 | 5/2009 | Huang et al. | |
| 2009/0128834 A1 | 5/2009 | Matsuhira | |
| 2010/0079356 A1 | 4/2010 | Hoellwarth | |
| 2010/0254017 A1* | 10/2010 | Martins | G02B 7/002 359/631 |
| 2010/0277471 A1 | 11/2010 | Beato et al. | |
| 2011/0043644 A1 | 2/2011 | Munger et al. | |
| 2012/0068913 A1 | 3/2012 | Bar-Zeev et al. | |
| 2012/0200595 A1 | 8/2012 | Lewis et al. | |
| 2012/0281181 A1 | 11/2012 | Chen et al. | |
| 2012/0326948 A1* | 12/2012 | Crocco | G09G 5/00 359/630 |
| 2013/0099700 A1* | 4/2013 | Kreye | H05B 47/10 315/320 |
| 2013/0155507 A1 | 6/2013 | Ryu et al. | |
| 2013/0162673 A1 | 6/2013 | Bohn | |
| 2013/0194254 A1 | 8/2013 | Miyoshi et al. | |
| 2013/0215147 A1 | 8/2013 | Hilkes et al. | |
| 2013/0329184 A1 | 12/2013 | Barzak et al. | |
| 2013/0329190 A1 | 12/2013 | Lewis et al. | |
| 2013/0335543 A1 | 12/2013 | Hilkes et al. | |
| 2014/0002587 A1* | 1/2014 | Aguren | H04N 5/23238 348/46 |
| 2014/0063054 A1* | 3/2014 | Osterhout | G06F 3/005 345/633 |
| 2014/0098226 A1 | 4/2014 | Pletcher | |
| 2014/0214122 A1 | 7/2014 | Nanduri et al. | |
| 2014/0232645 A1 | 8/2014 | Ali et al. | |
| 2014/0243971 A1 | 8/2014 | Pugh et al. | |
| 2014/0275760 A1* | 9/2014 | Lee | A61B 90/94 600/102 |
| 2014/0306866 A1 | 10/2014 | Miller et al. | |
| 2015/0084841 A1 | 3/2015 | Hilkes | |
| 2015/0193984 A1 | 7/2015 | Bar-Zeev et al. | |
| 2015/0205132 A1* | 7/2015 | Osterhout | G06F 3/013 345/633 |
| 2015/0355481 A1 | 12/2015 | Hilkes et al. | |
| 2015/0362733 A1 | 12/2015 | Spivack | |
| 2015/0378074 A1 | 12/2015 | Kollin et al. | |
| 2016/0027216 A1 | 1/2016 | da Veiga et al. | |
| 2016/0037849 A1 | 2/2016 | Shearman et al. | |
| 2016/0055822 A1 | 2/2016 | Bell | |
| 2016/0183779 A1* | 6/2016 | Ren | A61B 3/0058 351/246 |
| 2016/0196694 A1 | 7/2016 | Lindeman | |
| 2016/0267720 A1 | 9/2016 | Mandella et al. | |
| 2016/0270648 A1 | 9/2016 | Freeman et al. | |
| 2016/0377871 A1 | 12/2016 | Kress et al. | |
| 2016/0379593 A1 | 12/2016 | Borenstein et al. | |
| 2017/0010469 A1 | 1/2017 | Samec et al. | |
| 2017/0068119 A1 | 3/2017 | Antaki et al. | |
| 2017/0236332 A1 | 8/2017 | Kipman et al. | |
| 2017/0242253 A1 | 8/2017 | Benesh | |
| 2017/0323615 A1 | 11/2017 | Hazra et al. | |
| 2018/0045964 A1 | 2/2018 | Jones et al. | |
| 2018/0325618 A1 | 11/2018 | Justin et al. | |
| 2019/0339528 A1 | 11/2019 | Freeman et al. | |

OTHER PUBLICATIONS

KIPO, "International Search Report", dated Jul. 31, 2018, Published in: WO.
KIPO, "International Search Report", dated Oct. 28, 2019, Published in: WO.
KIPO, "International Search Report", dated Nov. 11, 2019, Published in: WO.
Loshin et al., "The Programmable Remapper: Clinical Applications for Patients With Field Defects", "Optometry and Vision Science", Nov. 4, 1988, pp. 389-395, vol. 66, No. 6.
Wrobleswki et al., "Testing of Visual Field With Virtual Reality Goggles in Manual and Visual Grasp Modes", "http://www.hindawi.com/journals/bmri/2014/206082", Jan. 1, 2014, pp. 1-7, vol. 2014, No. 206082, Publisher: Biomed Research International.
International Search Report and Written Opinion (International PCT Patent Application No. PCT/US2020/053098) dated Jan. 13, 2021.
European Search Report and Written Opinion (European Patent Application No. 18790963.5); dated Jan. 11, 2021.
Korean Intellectual Property Office; International Search Report and Written Opinion; dated Jun. 15, 2021.

* cited by examiner

MULTI-OPTION ALL-DIGITAL 3D SURGERY VISUALIZATION SYSTEM AND CONTROL

CROSS REFERENCE

This application is based on and claims priority to U.S. Provisional Patent Application No. 62/979,999 filed Feb. 21, 2020, U.S. Provisional Patent Application No. 62/986,461 filed Mar. 6, 2020, U.S. Provisional Patent Application No. 63/005,202 filed Apr. 3, 2020, and U.S. Provisional Patent Application No. 63/019,796 filed May 4, 2020. It is also a continuation-in-part of U.S. patent application Ser. No. 15/073,144 filed Mar. 17, 2016, which issued on May 1, 2018 as U.S. Pat. No. 9,955,862, U.S. patent application Ser. No. 15/940,561 filed Mar. 29, 2018, which issued on Oct. 30, 2018 as U.S. Pat. No. 10,111,583, U.S. patent application Ser. No. 16/173,719 filed Oct. 29, 2018, which issued as U.S. Pat. No. 10,874,297 on Dec. 29, 2020, U.S. patent application Ser. No. 17/137,069 filed Dec. 29, 2020, U.S. patent application Ser. No. 17/137,093 filed Dec. 29, 2020, and U.S. patent application Ser. No. 17/151,174 filed Jan. 17, 2021, all of which claim the benefit of U.S. Provisional Patent Application No. 62/134,422 filed Mar. 17, 2015; of U.S. patent application Ser. No. 15/962,661 filed Apr. 25, 2018, which claims the benefit of U.S. Provisional Patent Application No. 62/489,801 filed Apr. 25, 2017; of U.S. patent application Ser. No. 16/511,202 filed Jul. 15, 2019, which claims the benefit of U.S. Provisional Patent Application No. 62/697,854 filed Jul. 13, 2018; of U.S. patent application Ser. No. 16/511,451 filed Jul. 15, 2019; and of U.S. patent application Ser. No. 17/034,944 filed Sep. 28, 2020, which claims the benefit of U.S. Provisional Patent Application No. 62/907,300 filed Sep. 27, 2019. All are incorporated herein by reference.

COPYRIGHT NOTICE

A portion of this disclosure contains material that is subject to copyright or trademark protection. The copyright and trademark owner has no objection to the facsimile reproduction by anyone of this patent document as it appears in the U.S. Patent and Trademark Office, patent file or records, but reserves all copyrights whatsoever in the subject matter presented herein. The trademark names of the systems herein are those selected by the inventors but are not exclusive of names which could be used.

BACKGROUND OF THE INVENTION

Field of the Invention

This invention relates generally to an all-digital multi-option 3D surgery visualization system (ADMO3DV), and more particularly, but not by way of limitation, to augmented and extended reality glasses for use in surgery visualization, with the additional option of viewing 3D on an autostereoscopic monitor, or a DOS3DV combined with a digital 3D stereoscopic and a model controller system incorporating a wired and wireless information transfer system.

Description of the Related Art

There is a need for surgeons to be able to access real-time and pre-recorded computer-generated and/or camera images in the operating room. In addition, the operating room (OR) healthcare professionals need multiple viewing ports providing 3D surgery site information to such personnel for them to accomplish their OR tasks. Since the 1800's, surgeons have relied on the standard optical microscope (SOM), which uses multiple lenses in a dual tube configuration to create optical zoom and magnification. OR personnel also need to be able to recall electronic medical record (EMR) information during surgery, such as 3D MRI's, CT scans, and other imaging, which currently is done through 2D viewing on multiple monitors throughout the OR. In the recent past, some large medical device manufactures have introduced SOM's that project through a wired connection onto 3D monitor's which require the OR personnel to wear polarized 3D glasses and which require the surgeon to strain, crane, or lean for hours to observe. This is somewhat akin to having a surgeon wearing sunglasses to a surgery, and does not provide the surgeon with good ergonomics or state-of-the-art digital technologies.

Recent trends in the field have shown some SOM manufacturers adding digital imaging to the legacy equipment, but this means that an already large SOM becomes larger and more cumbersome, and take ever larger highly-valued surgery space away from the OR personnel. The SOM systems have the advantage of offering an ocular only view or a digital view; however, the result constrains the surgeon to forced unergonomic positions for hours of surgery use, often causing neck, back, hip, and hamstring straining. Many surgeons find they have to retire early due to such stress and strain, or must undergo surgery themselves to alleviate work-related musculoskeletal eisorders (WMSDs), which are prevalent among surgeons and often result in practice modification.

Some medical investigations show that WMSD's exist in as much as 66% to 94% of surgeons practicing open surgeries, with surgeons showing 73% to 100% WMSD's for conventional laparoscopic surgeries, and a rate of 54% to 87% for vaginal surgeries, and 23% to 80% of WMSD's reported from surgeons involved in robotic-assisted surgery.

Risk factors for WMSD's include use of loupes, headlamps, and SOM microscopes. Moreover, the huge space which is needed compromises the surgeon's ability to view digitally or have the space needed for positioning during surgery. With one report concluding that: "Future research must aim to develop objective surgical ergonomics instruments and guidelines and to correlate ergonomics assessments with pain and tissue-level damage in surgeons with WMSDs. Ergonomics training should be developed to protect surgeons from preventable, potentially career-altering injuries." (Catanzarite T, Tan-Kim J, Whitcomb EL, Menefee S. Ergonomics in Surgery: A Review. Female Pelvic Med Reconstr Surg. 2018 January/February; 24(1):1-12. doi: 10.1097/SPV.0000000000000456. PMID: 28914699.)

Thus, the legacy systems and their add-ons have not provided the OR personnel with the best state-of-the-art in digital 3D technologies and better ergonomics that are provided by employing the multi-option fully digital 3D surgical system as set out herein.

Others have attempted to employ virtual reality (VR) surgical or diagnostic headsets. However, a VR headset totally immerses the user into the images presented, essentially totally blocking and replacing the user's field of vision of the real-world, often called the real-reality (RR), with virtual images and the impossibility to see the virtual image and the RR around the OR personnel. Such systems are defined by their replacement of the reality around the user with a total virtual substitute. This immersion locks the surgeon into a virtual space that is not easy to extract from in case of emergency. The invention viewing option disclosed following transverses these limitations.

Such existing virtual reality surgery systems are generally uncomfortable and must be worn tight on the head, blocking out reality. VR systems seal out real-word light, sound, and air around the surgeon's eyes and cheeks, making the device hot and uncomfortable. The heat generated by the surgeon wearing the VR headset and from the headset itself often causes condensation on the interior lenses, which makes the images appear foggy and requires the surgeon to take of the VR headset for cleaning during the surgery. Clearing the lenses typically only helps temporarily. Some such systems use a trackpad that is turned 90 degrees from the user interface, so that swiping forward actually moves right and swiping backward moves left. This can be frustrating for the user, particularly if the user is left-handed. Moreover, typing within a VR headset menu is a painstaking and time-consuming chore, making entering HIPPA compliant passwords for sensitive data difficult. Furthermore, such virtual reality systems are typically heavy, with most of the weight forward on the head, making it uncomfortable for the user.

To address these concerns, augmented/extended reality (AXR) surgical systems have been introduced for surgical use. Whereas virtual reality immerses the user into the images presented and closes RR, AXR permits the surgeon, nurse, assistant, or tech user to see RR and what is actually happening in the user's world and then adds computer-generated, computer-manipulated, or secondary camera images to RR. Thus, while virtual reality completely covers and replaces the user's field-of-vision with virtual images, augmented/extended reality provides the user with vision of the real-world plus an overlay of computer-generated and/or manipulated photographic imagery or video ("virtual") images, which positions the user in the RR with virtual images added.

In an operating environment, an augmented/extended reality system permits the surgeon to both view and have magnified the virtual image or area of operation, while still having a sense of the operating or diagnostic room and being with all the other things happening in that space. The problem with current AXR surgical systems is that they offer a small field of vision on a heavy wearable that is often tethered to the system by a large cord, limiting the surgeon's movements and putting strain on the surgeon's neck and back. Furthermore, current AXR surgical systems must block out a great deal of ambient light to make the AXR images visible and are difficult to see in daylight or highly-lighted conditions, making the systems function more like a virtual reality system than an AXR system.

Based on the foregoing, it is desirable to provide a true AXR surgery system that provides an overlay of computer-generated images while maintaining a sufficient real-world view. Specifically, it is desirable to use an AXR headset which is a wearable pupil-forming display apparatus, comprised of two axially symmetric pupil expanding ocular engine with a folded prism so that the displays, which are the warmest electronic in the headset is the furthers away from the wearer's head and body.

It is further desirable for the system to be lightweight, comfortable, untethered, and is feature- and user-friendly It is further desirable for the system to offer a wide field of vision.

While the focus of this invention is on its application to the medical and surgery fields, it is further desirable for the same techniques to be utilized in other sectors while wearing a lightweight, comfortable, untethered, feature- and user-friendly AXR headset would be of benefit. Further, the surgery visualization system presented herein provides other viewing options besides the AXR wireless headset, such as (i) a autostereoscopic monitor featuring lenticular lenses or parallax barrier which does not need polarized 3D glasses for the user to view the surgery image in 3D; (ii) a digital ocular stereoscopic 3D viewport (DOS3DV) device mounted on a cobotic arm which comes to the OR personnel and moves with user as his or her posture changes or slouches during surgery; and (iii) a digital stereo microscope featuring two full-frame sensors with large pixel size of 6 microns or more, providing as much as 69 billion possible colors, more than the eye can see, also mounted on a cobotic arm; and (iv) a computer and multiple methods of transmission including wire and wires video transmission together with a model controller to control the digital microscope and viewing options.

SUMMARY OF THE INVENTION

In general, in a first aspect, the invention relates to a multiple option surgical 3d viewing system comprising:
a) a wearable device comprising one or more micro-displays, one or more lenses, where the micro-displays are capable of projecting images onto the lenses, a head-tracking subsystem, and an eye-tracking subsystem; and a central processing unit in communication with and capable of controlling the micro-displays, lenses, head-tracking subsystem, and eye-tracking subsystem; and
b) an optional viewport system comprised of an autostereoscopic monitor, which by way of lenticular lenses or parallax barrier provides 3D viewing to a user without the need for 3D polarized glasses; and/or
c) an optional viewport DOS3DV system described herein, which is mounted on a cobotic arm so that the viewing is 3D when viewed binocularly, and so that the cobotic arm automatically adjust to the movement of the surgeon during surgery as commanded by the m;
d) a digital microscope camera with dual sensors which employ large pixels 6 um or higher, mounted on a cobotic arm which provides the surgery site 3D video feed to the three (3) 3D viewing "viewport" options; and
e) and a computer with a model control system which controls the camera and sends the 3D surgery video from the microscope to each of the three (3) viewing systems, either wired or wirelessly.

The system may be capable of displaying images on the AXR headset lenses with a position based on a user's head position as tracked by the head-tracking subsystem and the user's eye position as tracked by the eye-tracking subsystem, while allowing the user to see through the lenses where the images are not being projected.

The micro-displays may be organic light-emitting diodes. The micro-displays may have a midrange luminance and may emit at least 3,000 NITS per display. The micro-displays may emit light of sufficient luminance that the system has an eye value of 300 to 500 NITS.

Each of the lenses may comprise: an inner layer of polarized optical coating; a middle layer that is polarized; and an outer layer, where the outer layer is a pixelated layer controllable by software which induces shadowing where the images are being projected. The outer layer may comprise electrically switchable suspended particle smart glass based on chiral-numatics properties of cholesteric liquid crystal and where the outer layer is not polarized. The inner layer may comprise a semi-spherical combiner.

The ADMO3DV surgical system may further comprise a digital microscope, with two camera sensors to create a 3D image to display on one or more of the three (3) viewing options where the images are obtained from said digital microscope. The one or more lenses may each comprise an aspheric lens. The lenses may be capable of keystoning software distortion correction.

Alternatively, the surgery site video can be obtained by the two image sensors mounted on the AXR headset. In this case, the cameras can either be mounted so that they see straight ahead in the line-of-sight that the eyes of the wearer would see, or the cameras can rotate on axis powered by an actuator, when commanded by the user providing the user with a downward view, even when the user's head is still in a comfortable alignment with the body and looking more or less straight ahead. In this fashion, a surgeon, such as a spine surgeon, can avoid the un-ergonomic situation of having to wear loupes on his head (which provide magnification), but requires the surgeon to put his chin against or close to his chest in a straining a bad ergonomic posture for the hours a surgery lasts.

The ADMO3DV surgical system may further comprise a six-degrees-of-freedom subsystem capable of pinning the images to a virtual marker in virtual space. The six-degrees-of-freedom subsystem may comprise a high-performance tracking system driven by multiple sensors and cameras.

The wearable device may have a visor design such that the one or more lenses provide both peripheral and downward viewing beyond the lens. The one or more lenses may be capable of being folded over or away from a user's head.

Figure 1:
FIG. 1 is a perspective view of the AXR surgical system in use.

Other advantages and features will be apparent from the following description and from the claims.

DETAILED DESCRIPTION OF THE INVENTION

The devices and methods discussed herein are merely illustrative of specific manners in which to make and use this invention and are not to be interpreted as limiting in scope.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification.

"Augmented and Extended Reality" (AXR) is defined herein in its common scientific use, which may include an interactive experience typically in a see-through headset with lenses of a real-world environment where the objects that reside in the real world are enhanced by computer-generated perceptual images and information, sometimes across multiple sensory modalities, including visual, auditory, haptic technologies, somatosensory, and/or olfactory.

"Extended Reality" is defined in its common scientific use, which is typically an umbrella term encapsulating augmented reality (AR) and/or virtual reality (VR) and/or mixed reality (MR) and/or real reality (RR) and everything in between. It may also include combined environments and human-machine interactions generated by computer technology such as 6DoF and SLAM, and artificial intelligence (AI), including machine learning (ML), where the 'X' represents a variable for any current or future spatial computing technologies, including digital content of any sort; for instance, in the medical field, a 3D MRI or CT scan images or data visualizations, like patient vitals, superimposed on an AR headset.

"Artificial Intelligence" (AI), sometimes called "Machine Learning" (ML), is used herein in its common scientific meaning, including referring to the simulation of human intelligence in machines that are programmed to think like humans and mimic their actions and decisions. The term may also be applied to an augmented reality headset that exhibits traits associated with a human mind, such as learning and/or problem-solving. AI may enable AR to interact with the physical environment in a multidimensional way. For instance, AI may permit object recognition and tracking, gestural input, eye-tracking, and voice command recognition to combine to let the user manipulate 2D and 3D objects in virtual space with the user's hands, eyes, and/or words.

"Cobotic" is used herein in its common scientific meaning, including a robotic function which is pre-programed and automatic, and human control, which augments the pre-programmed function. For instance, a cobotic arm could be set from "repose" position to fully extend, however the extension is augmented and guided by one or more of: facial recognition, eye-tracking, head-tracking, hand gesturing technology, verbal command, manual command, time-of-flight, dept perception, SLAM and Object Recognition, and 6DoF (the cobotic arm knows where it exists in the world). It can operate on a relative coordinate system that tells it where to go; where to be stored on "repose"; and directs its travel to the user's preferred use position, based on user preference settings. However, a user can manually take control, which shuts off the end-point of the automatic control, and it responds to the manual placement by the user. Then, as the user begins to re-position, slumps, or adjusts, the cobotic arm carries the DOS3DV instrument with the re-adjustment of the user position so that good ergonomics are always maintained.

The term "image(s)" or "virtual image(s) or "imaging" or "virtual objects" or "AXR imaging" is defined for the purpose of this patent as visualization of either 2D images or video or 3D images or video. The definition also includes the concept that one or more 2D images can be viewed in stereoscopy to create one or more virtual 3D perspectives. Further included in the "image(s)" definition, herein, is the idea that AXR 3D models may be viewed as a single or series of 2D images, as in a still picture or video, or a single or series of stereoscopic 3D images, as in a 3D images or video. The 3D effect may be created in the AXR headset by using an off-set paired perspective of a 3D model. In addition, 3D models in AXR can be viewed from different perspectives by the user or multiple users can view the same image from multiple perspectives.

The term "wireless" as used herein means the electromagnetic transfer of information between two or more points which are not connected by an electrical conductor, or a communication by technologies, such as light, magnetic, or electric fields, or the use of sound. The term "wired" communication as used herein includes all methods of wireline communication including, but not limited to, directly connected devices, telephone networks, ethernet connections, cable networks, internet access, fiber-optic communications, and waveguide (electromagnetism) connections.

The following are sensing and control technologies which may be utilized by the ADMO3DV system:

"Six Degrees of Freedom" (6DoF) is defined herein in its common meaning, including the way virtual objects can be moved in virtual space in AR. There are six total degrees of freedom in placing virtual images in AR. Three (3) correspond to rotational movement around the x, y, and z axes, commonly termed pitch, yaw, and roll. The other three (3) correspond to translational movement along those axes, which can be thought of as moving forward or backward, moving left or right, and moving up or down.

"Inertial Measurement Units" is used herein in its common scientific meaning, including referencing devices for measuring rotational movements, such as an accelerometer, a gyroscope, and a magnetometer, all located within the AXR headset. These IMUs may measure the headset's velocity, orientation, and gravitational forces to infer rotational orientation and movement.

"Haptic technologies" is used herein in its common scientific meaning and is sometimes called kinaesthetic communication or 3D touch. It may also refer to any technology which may create an experience of touch by applying forces, vibrations, or motions to the user or to an object. Haptics may enable users to feel the sense of touch via vibrations of forced motion. Haptic technologies can be used to create virtual objects in a computer simulation or virtual space, or to control those virtual objects, and may be used to enhance remote control of machines and devices (telerobotics). Haptic devices may incorporate tactile sensors that measure forces exerted by the user on the interface. This technology may employ touch sensors for control.

"Object Recognition" (OR) or "Object Identification" (OI) is used herein in its common scientific meaning, including a computer vision technique for identifying objects in images or videos. Object recognition may be a key output of deep learning and AI algorithms. When humans look at a photograph or watch a video, we can readily spot people, objects, scenes, and visual details. OR/OI does this from visual analysis based on a neural network algorithms reconciliation with pre-existing information.

"Simultaneous Localization and Mapping" (SLAM) is used herein in its common scientific meaning, including a technology that understands the physical world through a 3D grid of feature points. SLAM maps what the camera and sensors see in three dimensions with correct spatial information and distancing. This may make it possible for AXR applications to recognize RR 3D objects and scenes, as well as to instantly track motion in the RR, and to overlay digital interactive augmentations. SLAM incorporates the application of sensors sensing dept, time-of-flight, and creating a 3D grid. SLAM also incorporates infrared sensing and measurements.

The following terms relate to the virtual/augmented images on the AXR headset:

The term "lux" is the SI derived unit of illuminance and luminous emittance, measuring luminous flux per unit area. It is equal to one lumen per square meter.

The term "lumen" is the SI derived unit of luminous flux, a measure of the total quality of visible light emitted by a source per unit of time.

The term "luminance" is a photometric measure of the luminous intensity per unit area of light traveling in a given direction. It describes the amount of light that passes through, is emitted from, or is reflected from a particular area, and falls within a given solid angle.

The term "candela" is the SI unit of luminous intensity. The candela per square meter is the derived SI unit of luminance. It is from the candela that we get the modern measurement of NIT, which is commonly referenced in wearable and cellular applications.

The term "NIT" is a non-SI name also used for the candela per square meter. As a measure of light emitted per unit area, this unit is frequently used to specify the brightness of a cellular or wearable display device. The sRGB spec for monitors targets 80 cd/m2. Typically, calibrated monitors should have a brightness of 120 cd/m2. As system described herein uses a NIT reference for its light/brightness measurements.

The AXR 3D Headset Technology.

In general, in a first aspect, the ADMO3DV system invention relates to an augmented and extended reality (AXR) surgical system option which can be either wired or typically the preferred wireless headset. The system may comprise a wearable device 1, such as a head mounted display (HMD) or glasses, that provides the user with virtual reality (VR), augmented reality (AR), and/or mixed-extended reality (XR) for surgery visualization, as shown in FIG. 1. This may allow the user to access 2D or 3D imaging, magnification, virtual visualization, six-degrees of freedom (6DoF) image and simultaneous localization and mapping (SLAM) management, and/or other images while still viewing real reality (RR) and thus maintaining a presence in the operating room.

Figure 2:
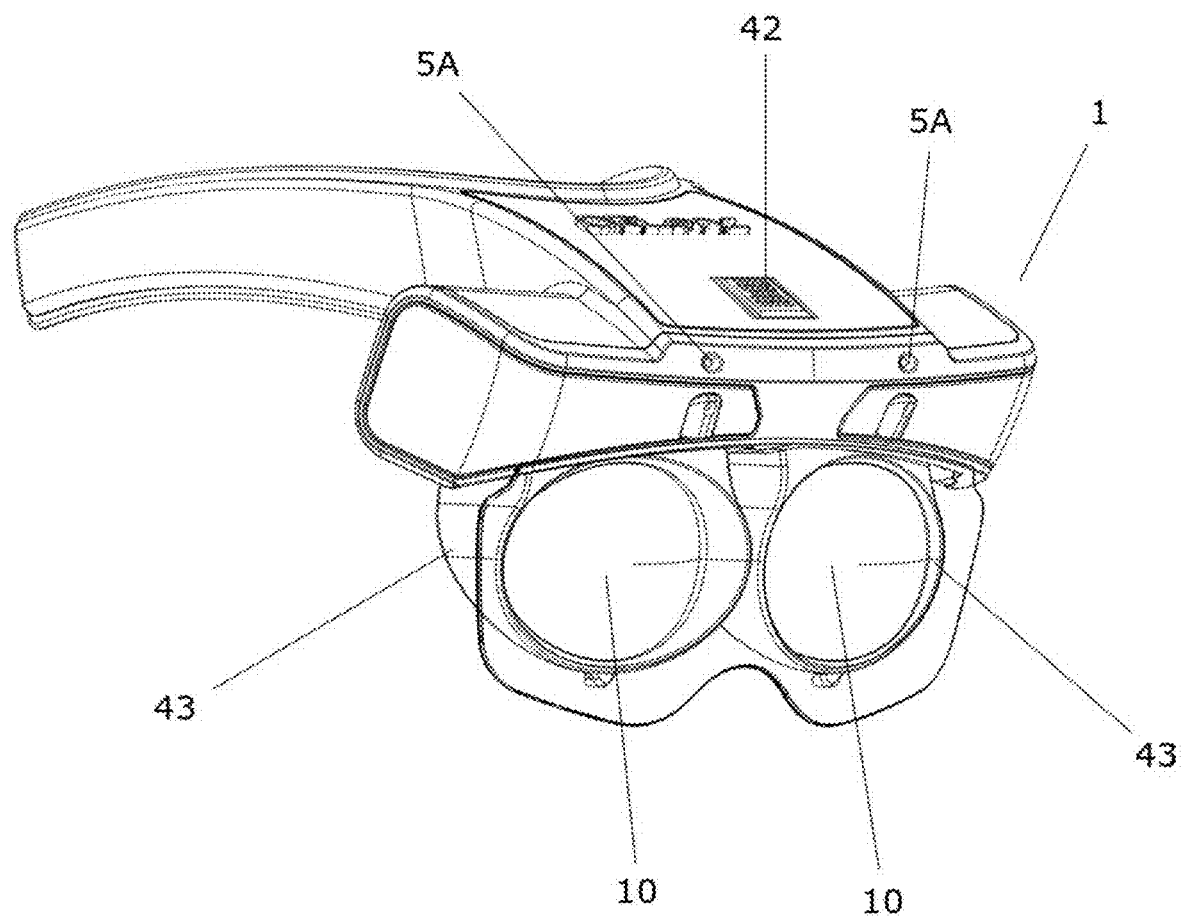
FIG. 2 is a perspective view of the AXR surgical system headset.
Figure 3:
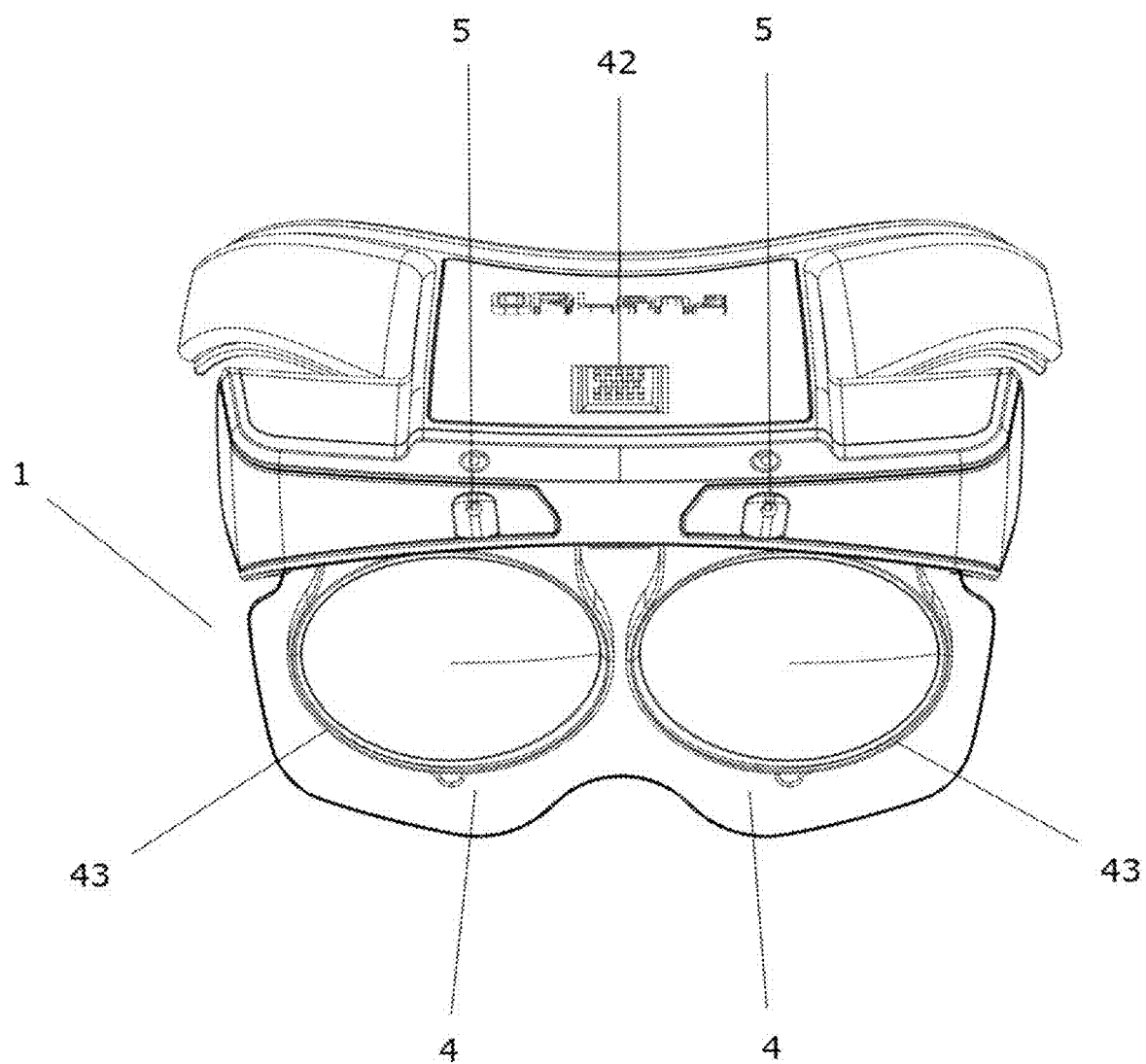
FIG. 3 is a front view of the AXR surgical system headset.

The AXR headset system may comprise one or more micro-displays 2, a head-tracking subsystem 3, an eye-tracking subsystem 4, and one or more cameras 5, all of which may be included on the wearable device 1. The system may further comprise one or more lenses 10, where the micro-displays 2 are capable of projecting images on the lenses 10, where the images may be reflected back to the user's eyes. For example, as shown in FIGS. 2 and 3, the wearable device 1 may be a head mounted display with a pair of lenses 10, one in front of each of the user's eyes. One or more micro-displays 2 may be located above the user's eyes and may be pointed toward the lenses 10. The cameras 5 may be 4K or higher each and may provide image input, while the head-tracking subsystem 3 and the eye-tracking subsystem 4 may provide positional input, allowing the system to project the desired images to the desired location for the user to view the images. Additional image input may be provided from other sources such as SLAM or other sensing cameras 5A. All components may be controlled by a CPU, which may be located on the wearable device 1 or remotely. Other components may include additional central processing units, one or more graphics processing units, one or more digital signal processors, firmware, hardware, software, and/or memory components, as well as other desired components, including a non-transitory model view controller. The high-level components may control the features and functions of the AXR headset 1, including, but not limited to, its cameras 5, micro-displays 2, lenses 10, sensors, communications, and sub systems.

Among virtual image display solutions for AXR viewing are catadioptric optics which are preferred in that they employ a partially transmissive curved mirror for directing image-bearing light to the viewer's eye and a partially reflective beam splitter for combining light generated at a 2D display with the real-world visible scene, which forms a superior 3D image and holographic images when viewed binocularly.

The headset may be wireless or wired. If wireless, the wireless module antenna may be connected to the main circuit board inside the headset and may radiate RF to the outside world through the WiFi, cellular, or 5G antennae 42.

The AXR headset may contain a small worm gear or similar device connected to the two lens frames 43, which may move closer and farther, approximately 5 mm, in order to adjust for interpupillary distance (IPD) for each person. This may be accomplished by the worm gear being connected to a spindle gear threaded on both ends, which may connect to the lens frames, which may be on a track that permits them this measure of movement. A remote Bluetooth connection may be housed in the charging station drawers, where it can automatically adjust based on the information preprogrammed into the ADMO3DV controller according to each user's IPD or can be accomplished manually through a small Bluetooth handheld device housed in each drawer and independently connected and secured to each device.

Figure 7:
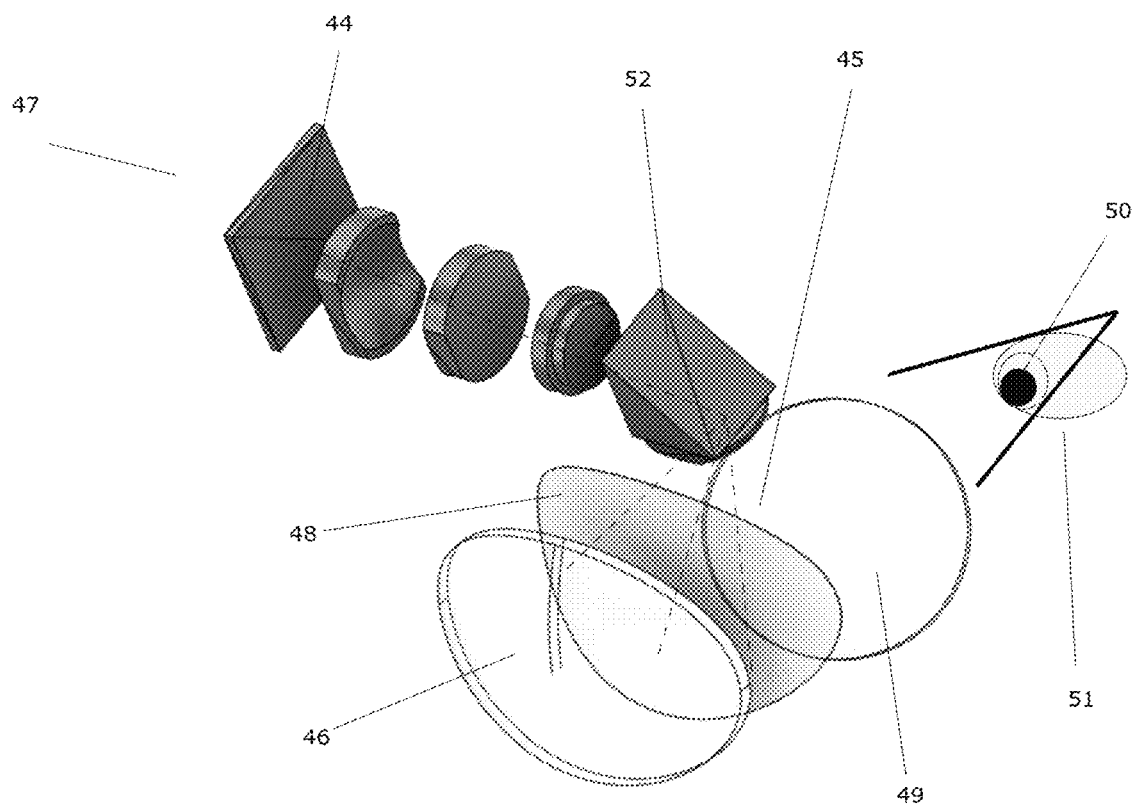
FIG. 7 is a break-out of the near-eye pupil-forming catadioptric optical engine in the AXR headset.

One such AXR headset, as shown in FIG. 7 and which may produce the best results for surgery, is an axially symmetric near-eye pupil-forming wearable AXR display apparatus comprising:

(i) relay of the image generator 44 to form a curved intermediate image 45 as a conjugate image. As a type of "aerial" image, intermediate image 45 may be formed in air, serving as the optical "object" for forming the virtual image. Intermediate image 45 may be formed along the curved focal surface of curved mirror 46, with the approximate aerial position shown by a dashed line in FIG. 7.

(ii) an optical relay 47, with particular structure as described in more detail subsequently, may conjugate the image formed from image generator 44 to the curved intermediate image 45 along the focal surface. Curved mirror 46 may be partially transmissive, such as between about 30% to 70% transmissive, for example, allowing visibility of the real-world object scene to the viewer. A nominal transmission range of 50 to 70% may be useful in many applications and the see-through may be increased with the use of brighter imaging source such as an LCD or other micro display.

(iii) use of a cylindrically curved quarter-wave plate (QWP) between mirror 48 and beam splitter 49. Curvature of this element may help to reduce variations of the retardation imparted to the image-bearing light by the QWP over the field of view.

(iv) large exit pupil 50. System optics can form a 10 mm exit pupil at the viewer's eye-box for eye 51. Forming a suitably sized pupil for the viewer may help to provide an eye box of reasonable dimensions to allow eye movement, without noticeable vignetting. Also, an enlarged eye box may permit the headset to move or slip without noticeable degradation of the viewed image(s). The apparatus may not need to provide pupil expansion, such as is used in existing wearable display apparatus, but may use pupil-forming optics for improved efficiency and brightness, as well as for improved image resolution.

Significantly, the eyes of the viewer may clearly see and be seen by others, with minimal impediment from the beam splitter and curved mirror optics that provide the electronically generated virtual image.

With the optical arrangement shown, the aperture stop AS may lie within prism 52 of the image relay, along or near the fold surface that is provided. This arrangement may be advantageous for component packaging and spacing, allowing pris to be reduced in size over other configurations using a folding prism.

The given design may allow an FOV along the horizontal (x) axis, the axis parallel to a line between left and right pupils of the viewer's eyes, of greater than 50 degrees. The FOV aspect ratio (horizontal:vertical) may equal or exceeds 1.5. Digital correction may not be needed for distortion or lateral color.

According to an embodiment, curved reflector 46 may have a conic surface shape. The conic shape is advantaged, in the embodiment shown herein, helping to control chief ray angles, thus correcting for distortion. Depending on whether or not polarization is used for configuring light paths, beam splitter 49 can be either a polarization-neutral beam splitter or a polarization beam splitter. Beam splitter 49 can be, for example, a wire grid polarization beam splitter as shown in FIG. 7.

Figure 5:
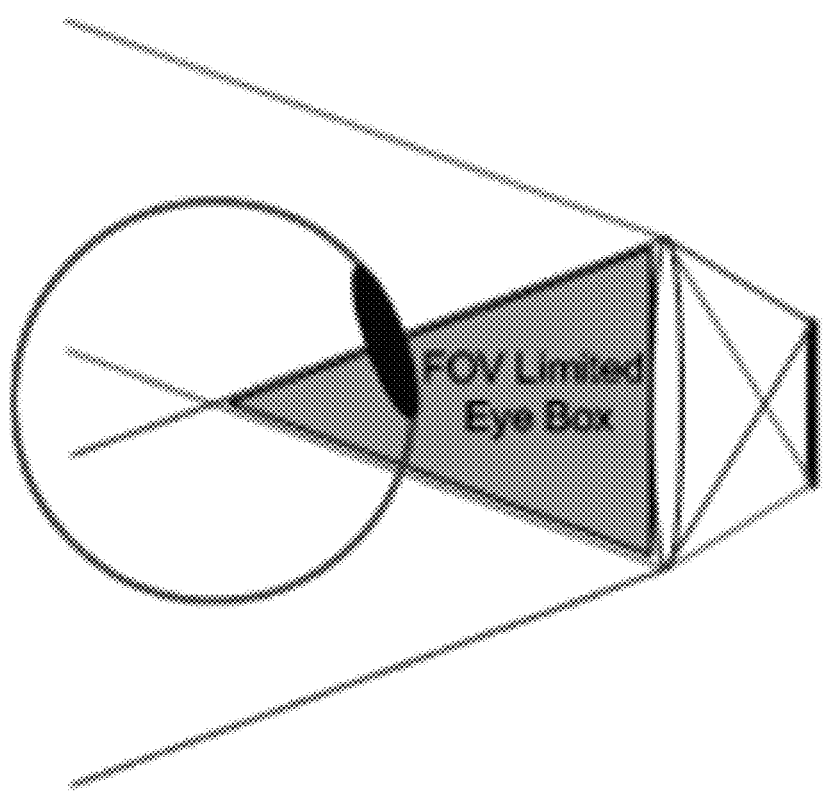
FIG. 5 is a diagrammatic illustration of an eye box.

The large field of vision of this above system may result in a large eye box for the user, as shown in FIG. 5. The eye box of any AXR or VR system may be crucial as it may serve as the connection between the device and the user. The eye box of the system may be large enough to provide comfortable viewing of the full field of vision with the highest resolution even if the headset moves while wearing. Further, the eye box of the system may be large enough to account for eye relief for the user, including allowances for brow size and how deep-set the user's eyes are, as well as clearance for eyeglasses and allowances for lateral pupil movement. As used herein, the term "eye box" is analogous to the term "eye relief" of a typical optical instrument, such as a telescope, a microscope, or binoculars, which is the distance from the last surface of an eyepiece within which the user's eye can obtain a full viewing angle. If a viewer's eye is outside this distance, a reduced field of view may be obtained. Thus, the smaller eye box of previous VR systems is inferior to the large eye box of the current system.

Figure 6:
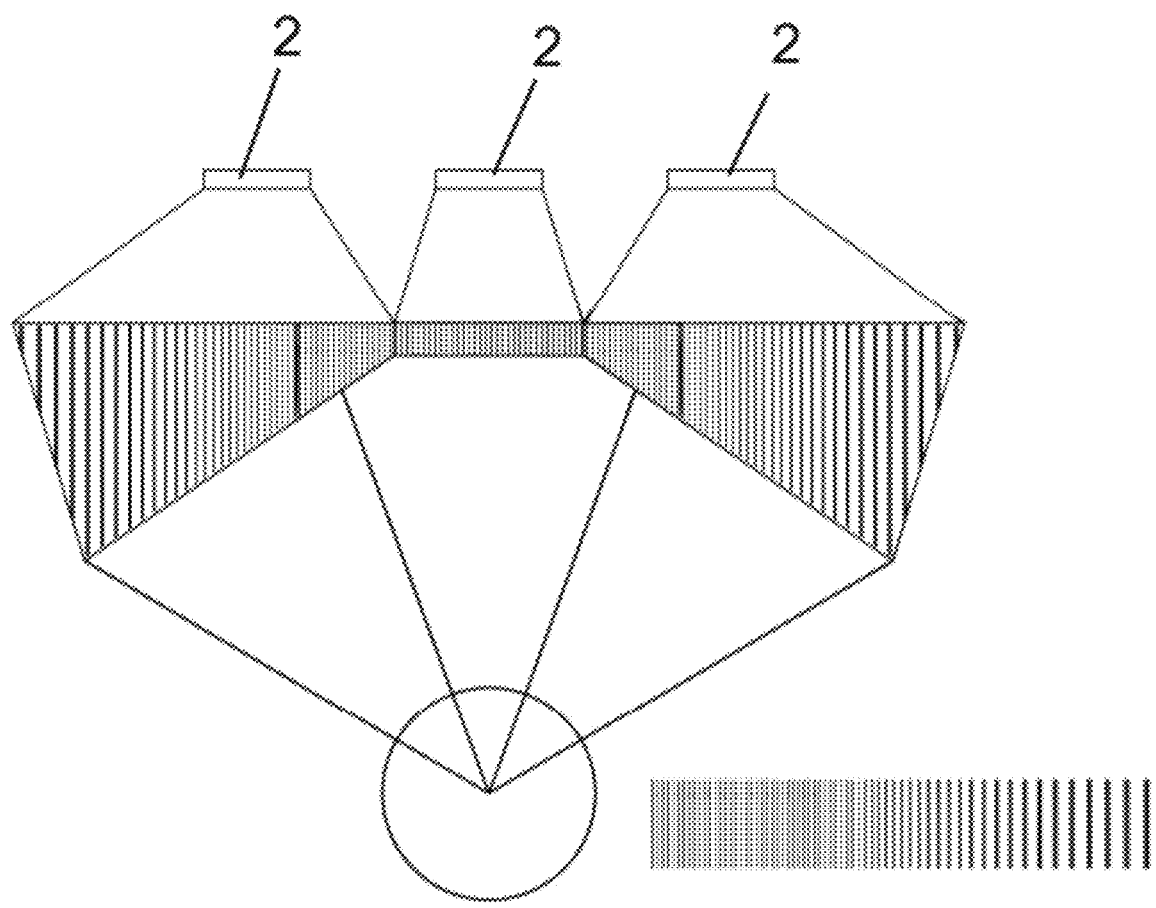
FIG. 6 is a diagrammatic view of the micro-displays.

Alternatively, an AXR headset may use a pupil expander mechanism such as will create an eye box of as much as 20×20 mm×60p/p/d. This may be achieved by providing three micro-displays 2 having the outer two displays 2 sharing pixels with the central display 2 through the system's algorithms, as shown in FIG. 6. To the foveal vision of the eye, where the highest resolution imagery is perceived on the retina, the system may present approximately 50 degrees horizontal by 20 degrees vertical field of vision at 60 pixels per degree. The remainder of the field of vision may have approximately 20 pixels per degree, which may be equal to or better than the acuity in the outer parts of the retina. The lenses 10 may be concave in construction, aiding to focus and enlarge the surgeon's eye pupil view for the biggest possible eye box. Thus, it is almost impossible for the user to lose the view of the AXR or surgery visualization image due to the large FOV and exceedingly high resolution of the system.

The AXR system may be capable of allowing the user's eye to rotate in order to view off axis field angles while still maintaining high resolution, either AR or RR, at approximately 50 pixels per degree. The optical engine in the system may accommodate not only large field of vision eye rotation, but also a translation of rotation of the pupil due to the fact that, in reality, the eye rotates about a point that is 10 mm behind the pupil, where the fovea actually exists. The optical engine may provide a no-chromatic distortion display providing resolution of 56-60 pixels per degree. The optical engine may use an aspheric catadioptric off-axis engine. The asphere's more complex surface profile may reduce or eliminate spherical aberration and also reduce other optical aberrations such as astigmatism, compared to a simple lens. A single aspheric lens may be capable of replacing a much more complex multi-lens system when used in combination with an ellipse reflecting lens collector. The resulting device may be smaller, lighter, and less expensive than a multi-lens design. Aspheric elements may be used in the lenses to reduce aberrations, and in combination with reflective elements (catadioptric systems) such as the aspherical Schmidt corrector plate used in the Schmidt cameras and the Schmidt-Cassegrain telescopes or ellipse collector optical cut.

Features of the AXR optical engine may include micro-display lens correction, optical collimators in more than one place, reflective lens correction to adjust the focal point for near eye projection, dynamic opacity to compensate for brightness overcoming light loss, keystoning software distortion correction, IPD mechanical and/or software adjustment per person, and an off-axis, semi-spherical (elliptical) combiner in the inner portion of the lens.

The resolution of the AXR micro-displays 2 may specifically be 22 pixels per degree, or 2560×1440 (Quad HD); 25 pixels per degree, at 3200×1440; 60 pixels per degree at 7200×1600; or any other desired resolution. The luminance may be 1,000 cd/m2, or higher, while contrast may be 100,000:1 or higher. The micro-displays 2 may support 110 percent of the sRGB color gamut ratio.

The micro-displays 2 may be organic light-emitting diodes (OLED or Organic LED), also known as organic electroluminescent (EL) diodes, which is a light-emitting diode in which the emissive electroluminescent layer is a film of organic compound that emits light in response to an electric current. This organic layer may be situated between two electrodes; typically, at least one of these electrodes is transparent. The micro-displays 2 of the system may each comprise a front plane and a semiconductor back plane manufactured by TSMC or XFAB connecting the multiple front-plane screens.

Luminance is often used to characterize emissions or reflection from flat, diffuse surfaces. Luminance levels indicate how much luminous power could be detected by the human eye looking at a particular micro-display surface from a particular angle or view. Luminance is thus an indicator of how bright the surface will appear. In this case, the solid angle of interest is the solid angle subtended by the eye's pupil. Luminance is used in the video industry to characterize the brightness of displays. A typical computer display emits between 50 and 300 cd/m$^2$. The sun has a luminance of about 1.6×109 cd/m$^2$ at noon. Luminance is invariant in geometric optics. This means that for an ideal optical system, the luminance at the output is the same as the input luminance. The system of the present invention may have a midrange luminance.

For passive AXR optical systems, the output luminance is at most equal to the input. As an example, if one uses a lens to form an image that is smaller than the source object, the luminous power is concentrated into a smaller area, meaning that the illuminance is higher at the image. The light at the image plane, however, fills a larger solid angle so the luminance comes out to be the same assuming there is no loss at the lens. Thus, the image can never be brighter than the source. However, when a TV or video projector is touted as able to output 1,000 Nits or Lumens, that does not mean that the TV or projector outputs that much light all the time. Frames or scenes most often display a range of bright and dark content, as well as a variation of colors. All these variations require different levels of light output which is accounted for in the algorithms of the system.

The AXR micro-displays may be capable of emitting as much as 3,000 NITs per display, currently, with plans to enhance this brightness in the future. With two of three displays together, as in the alternative example above, the overall brightness may be increased across the viewing area. While the two kinds of meters can actually measure either kind of light; NITS measurement, light emanating from a point (or emanating from an area, in the case of a screen) does not diminish with distance. Therefore, in considering the total brightness, the key is that the measurement Steradian of the measuring tool needs to cover the pertinent screen.

When the micro-display emits 1,000 NITS, the eye-box value may be 300 to 500 NITS, depending on the image material. This may be adjustable by the user. For reference, a TV is designed for 300 to 500 NITS, but a computer monitor is designed at only 200 NITS because it is assumed that you will be looking at it for hours on end and the desire is to reduce eye strain.

Thus, in addition to considerations of brightness, one must consider the imposition of an electronic darkening of the entire lens or electronic darkening of just the area in which the virtual image is contained pixel by pixel. This idea has been called dynamic opacity, which, when added to the optical engine, may also provide additional brightness to the augmented reality image by electronically darkening the RR around or behind the virtual image. By making the real world (RR) behind the augmented reality (AR) image on a gradient from 1% to 100% opaque, the dynamic opacity may provide an even greater luminance referred to the eye.

The AXR system may be capable of displaying both real reality and computer-generated images (CG or CGI) or computer captured and manipulated images (CMI), effectively creating the illusion of AXR. In this context, CMI may mean previously recorded, captured, or created images or video from a different reality than the RR displayed in the AXR headset. Additionally or alternately, the system may be capable of functioning as a "heads-up" system, allowing the user to look at the images on the micro-displays 2 or look beyond the display to the larger environment of the real-world operating room and attendants. Thus, the AXR system may provide a full field of vision, unlike existing systems. Specifically, for example, the micro-displays 2 may provide a wide field of vision of, for instance, 120 degrees, namely 60 degrees horizontal and 36 or more 65 degrees vertically in each eye, or other desired field of vision. This may allow a high angular resolution of 60 pixels per degree in the eye box, which is the highest resolution the eye can distinguish at 20/20. Humans have a slightly over 210-degree forward-facing arc of their visual field. The cameras 5 of the system may capture all or most of the human forward-facing degrees, when needed. Correspondingly, the user may view 120 degrees field-of-view (FOV) of AXR through the cameras 5 and micro-displays 2 and 210 degrees of RR with the system functioning as a heads-up display (HUD). This field of vision may actually be even larger from a practical standpoint as the user may, for example, look down at his or her hands, which are outside the AR/RR presented field of vision. The availability of viewing the RR environment may be important to a surgeon when he or she is trying to unfocus from the surgery site to a non-surgery site to pick up a tool or adjust his or her hands during surgery. This type of viewing is not possible with existing VR systems, which require the eye of the surgeon to be always exactly aligned, something that might well prove exhausting in a lengthy surgery.

The AXR cameras 5 may be two on-board 4K or higher resolution cameras and may, as noted above, capture a wide field-of-view, such as 180 to 210 degrees forward-facing vision. This oversampling of the field of vision may then be stored per frame and used in conjunction with the eye-tracking subsystem 4 to present the actual field of vision depending on the user's gaze. In this fashion, the system may use images from the entirety of the 180 degrees captured or a reduced sample of the entire captured cameras degrees FOV. The reduced sample may be based on eye-tracking and eye-gaze correspondently. As the system's eye-tracking follows the eye of the surgeon as his or her eyes move, the system may be able to provide a subset of imagery from the fully captured 200 or more degrees.

Figure 8:
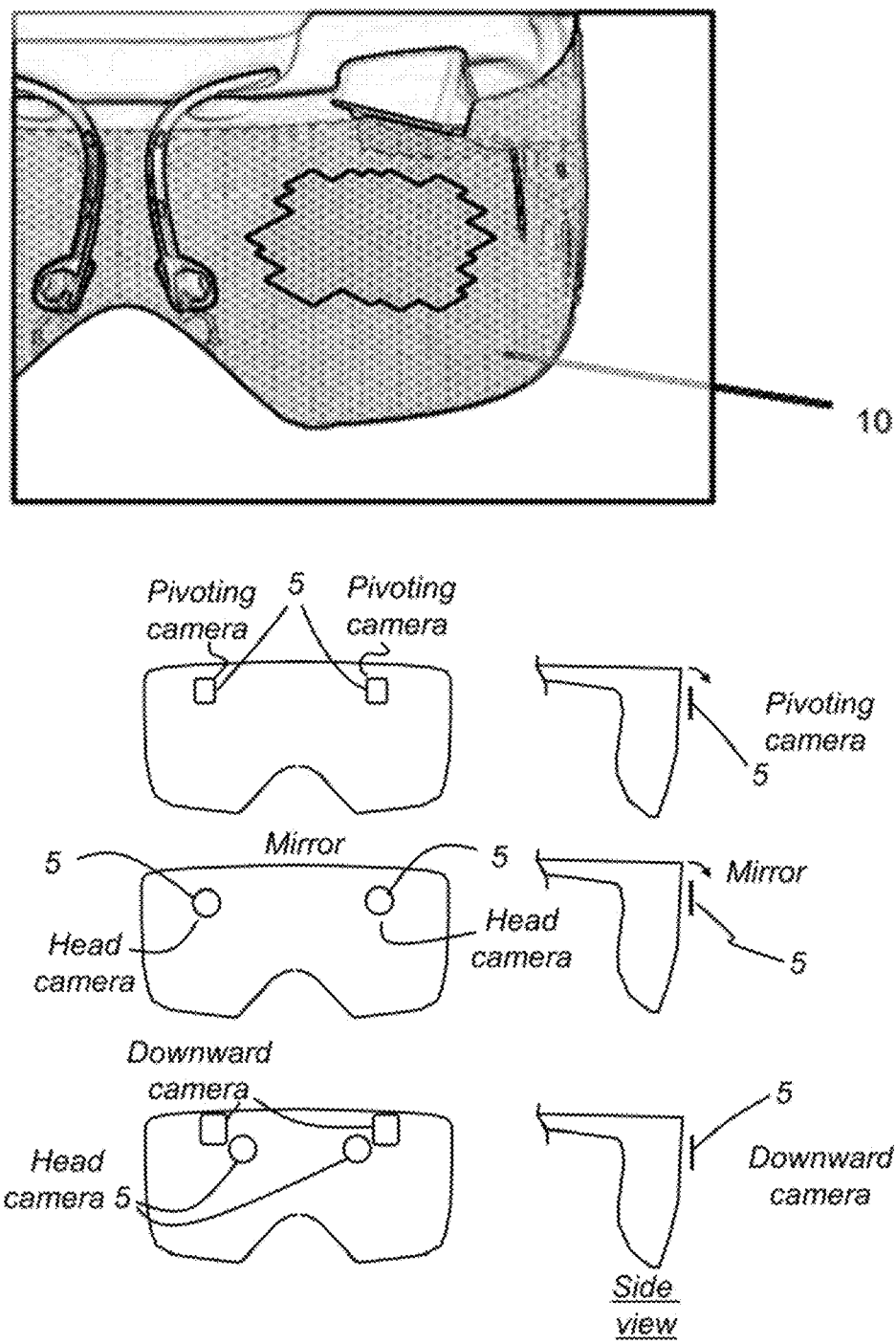
FIG. 8 is a close-up view of the dynamic opacity and the rotating articulation of the dual headset cameras up to 90 degrees.
Figure 9:
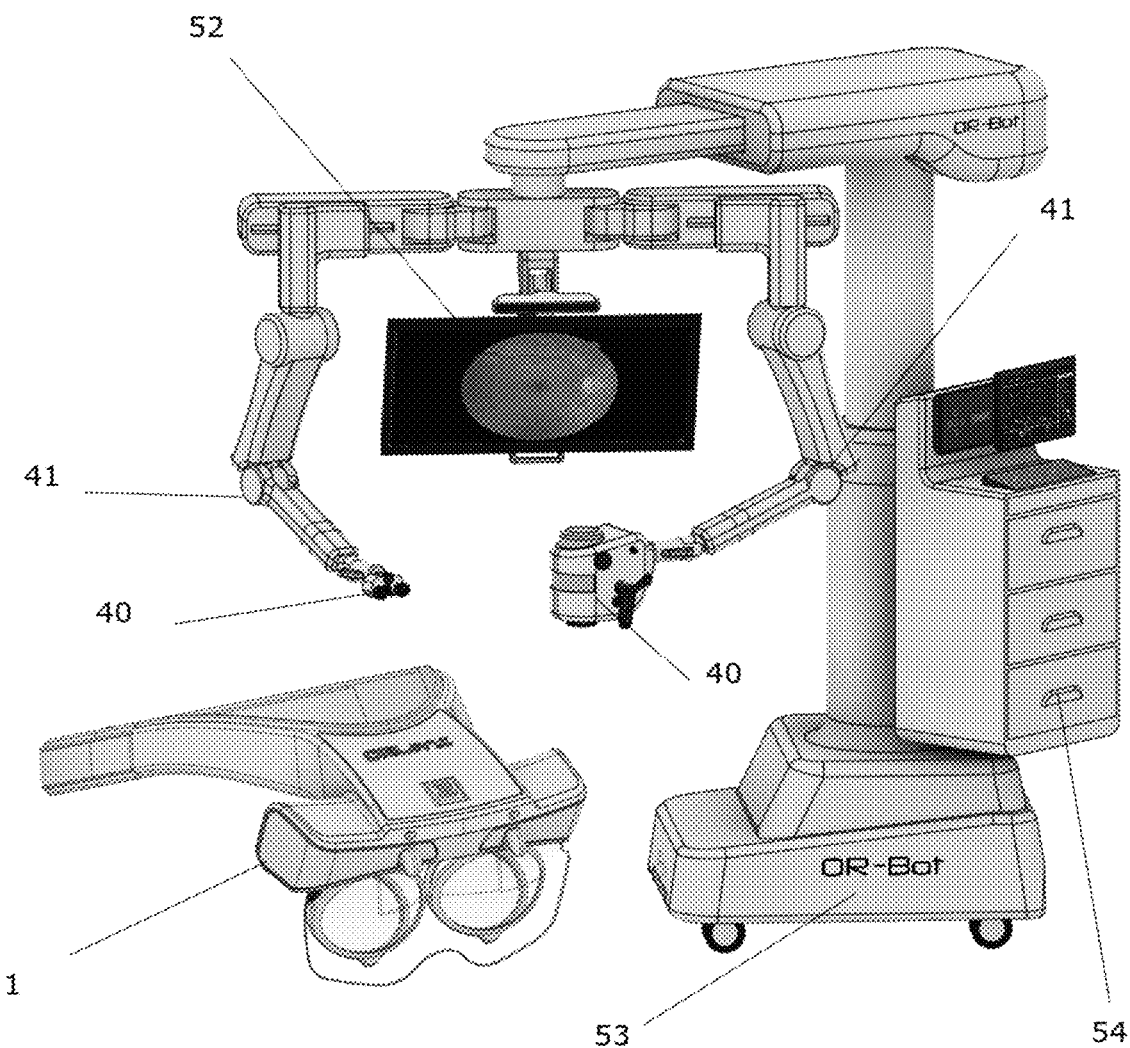
FIG. 9 is a view of the overall ADMO3DV surgery suite with its 3D microscope and three (3) 3D viewing options.
Figure 12:
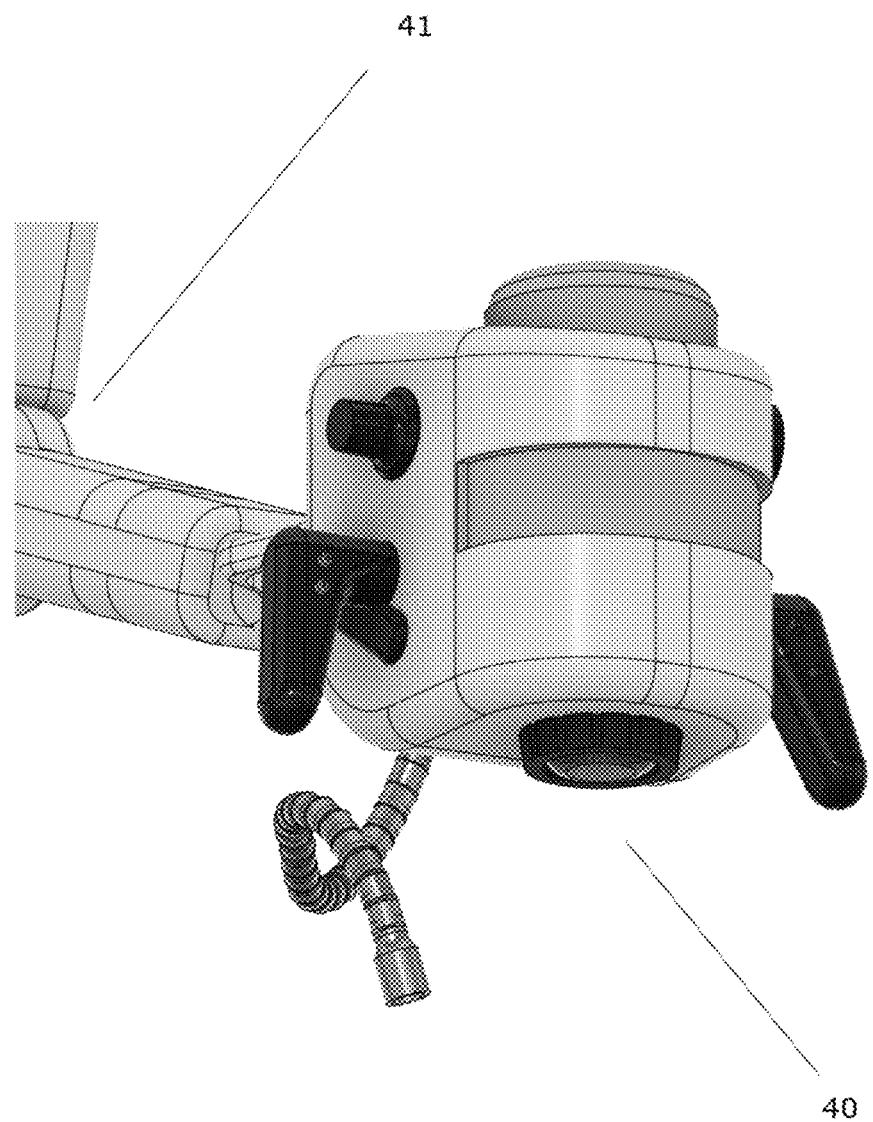
FIG. 12 is a diagrammatic view of the dual camera sensor microscope with internal and external lighting options.

The two AXR headset cameras FIG. 8 may be rotated up to 90 degrees on axis by voice command or virtual menu, or other control mechanism, which permits a user to look straight ahead with an ergonomic posture, moving and adjusting as necessary, while the cameras pivot to show a surgery view of a patient on a gurney between 60 to 90 degrees. The AXR headset in combination with the DCS3DM FIG. 12 provides up to 12 times zoom, two optical and 6 times digital zoom with no loss of resolution. The accelerometers, gyros, and magnetometers (IMUs) resident in the system's chipset may automatically enable and switch among the various video inputs depending on the position of the surgeons' head. When a surgeon looks down, the system may enable the front-facing cameras; when the surgeon looks up or straight ahead, the system may enable the downward cameras to permit the surgeon to comfortably find a looking-forward position where the downward-facing cameras capture the surgeon's hands and operating space. When a voice command is issued from the surgeon, the system may switch off the RR cameras and convert to projecting the images from a scope or digital microscope.

Alternatively, the virtual images projected by the micro-displays 2 may come from existing data, pictures, graphs, videos, MRI's, CT scans, or other pre-recorded images or information.

The one or more original source cameras may be mounted on the AXR headset 1 or as a part of an external cameral systems like the DCS3DM system described herein. Thus, the networked headsets and viewports ZZZZ of the system may allow multiple participants to see and experience the same surgery or diagnostic view or provide an experienced surgeon with the ability to remotely assist an immediately present or remote inexperienced surgeon. This technique may be used to also teach and train healthcare workers. By continually monitoring and transmitting the image of a surgery between two or more distant users, the system may enable remote virtual telemedicine collaboration between multiple surgeons, assistants, techs, students, or others.

The system may optionally exactly align the CG or GMI image with the real environment. This alignment may be accomplished by creating an overlay, which permits the alignment of preoperative CT or MRI 3D images with the currently treated patient's body, body parts, or internal organs. In this fashion, while wearing the AXR headset 1, the surgeon may be able to both view the whole person in RR while seeing images of internal items like the person's internal organs, blood, bone, or tissue while using 6DoF, SLAM, and gesturing recognition technologies or others techniques mentioned herein where the user can change the orientation and registry of the virtual image to match the real organ. The system may utilize dynamic opacity, described below, making the AXR image either a complete view, blocking RR and the real organ, or a partial transparency, where the AXR organ image or model and the RR organ can be viewed at the same time to align them together. In this fashion, surgery precision may be increased as the areas identified in the lab on the CT or MRI can be superimposed over the real organ to know exactly where to inject, incise, resect, or otherwise operate.

The dynamic opacity subsystem that allows the system to function as a true AXR system may be provided by a multilayered lens 10, which may be part of the wearable device 1. Typically, when using a reflected image on a see-through lens in sunlight or bright light conditions, the reflected image can be washed out. Other systems solve this problem with dark lenses. Having the lens shaded all the time, however, makes the wearer vulnerable to falling or tripping over unseen obstacles. The dynamic opacity of the lens 10 of the current system, however, may only obscure that portion of the lens 10 where the eyes are viewing the AXR image as alpha matte composites, meaning the combining of several images from different sources into a single image. FIG. 8 illustrates the dynamic opacity of the present system.

The system may utilize alpha matte software that works in conjunction with eye-tracking technology and software to map the user's eye gaze and adjust not only the image, but also move or vary the opacity of the exterior of the lens 10 where the eyes are gazing and the image is projected. In addition, the software may automatically or manually adjust the opaqueness of the alpha matte display up or down to meet ambient lighting conditions.

Figure 4:
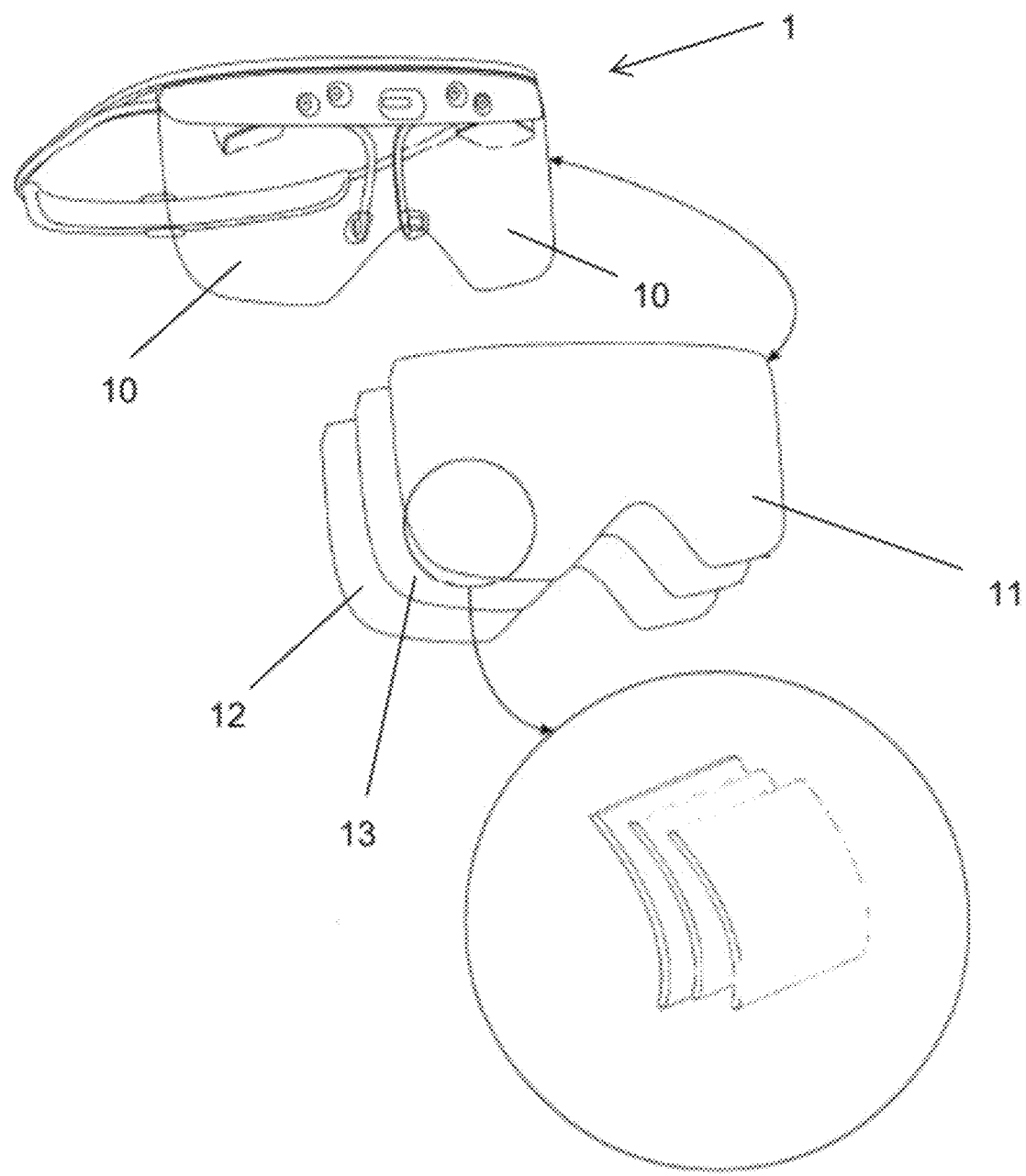
FIG. 4 is an exploded view of the lenses.

The lens 10 may have multiple layers, as shown in FIG. 4, with dynamic opacity provided on the outer layer 11, furthest from the user's eye. This layer 11 may be pixelated, which may permit the system to create a shadow or mirrored image of whatever virtual image is being displayed. This may provide a backdrop for the virtual image, blocking out light that might otherwise wash out the image. The remainder of the layer 11, where the image is not being displayed, may remain clear. Alternately, all of the pixels of the layer 11 may be activated, making the layer 11 fully obscure and blocking out the RR. This may allow the user to use the system as a VR-type headset, but with the ability to see his or her hands to pick up tools and instruments in the periphery of the glasses where the lens does not obscure the RR vision. Thus, surgeons who do not like surgery room distractions can chose to engage the dynamic opacity via voice command and make the system more like a VR headset, blocking out the view through the lens 10 behind the AXR image or video when ultra-concentration is needed. At other times, the surgeon can choose to make the dynamic opacity off or clear in the portion of the lens where there is no reflected image, to use the system in normal mode, where only the AXR image is shadowed form the back. The dynamic opacity of the lens 10 may provide a buffer between the displayed image and exterior light, giving the AXR image greater brightness to the eye. The system may allow the dynamic opacity to be enabled automatically, under pre-set conditions, manually, or with voice, gesture, or eye-tracking command.

In this fashion, the system may give the surgeon the highest RR visibility, and the added benefit of both AR and VR, so that the best of both types of altered reality is provided.

The layer 11 may comprise a plurality of pixels of cholesteric liquid crystal, each of which may be independently capable of becoming clear or opaque, or in between, as desired. In other words, the layer 11 may use electrically switchable suspended-particle smart glass based on the chiral-numatics properties of certain liquid crystals, which may not require a polarizer to achieve the alpha matte or opaqueness. The dynamic opacity, since it does not have to rely on a polarization layer, may provide gradation from and including zero to 100 percent, while it is a generally accepted scientific fact that LDC technology with polarizers can only become approximately 50% clear. This is because a system using embedded polarizers can never become 100% clear.

In suspended-particle devices (SPDs), like the layer 11, a thin film laminate of rod-like nano-scale particles may be suspended in a liquid and placed between two pieces of glass or plastic or attached to one layer without polarization or back-plane. When no voltage is applied, the suspended particles may be randomly organized, thus blocking and absorbing light. When voltage is applied, the suspended particles may align and let light pass. This dynamic opacity technology is bi-stable, and is therefore highly energy efficient because the cholesteric liquid crystals do not need power to maintain a selected state like most LCD technologies, which use twisted-numatics and always need power to maintain each level of a twisted-numatic state.

The lens 10 may further comprise a reflective layer 12, which may be a lens or a coating. The reflective layer 12 may be located closest to the user's eye and may be the surface upon which images projected by the micro-displays 2 for reflection back to the user's eyes. An anti-reflective layer 13 may be positioned next and may be a layer or optical coating that may prevent unwanted artifacts, such as ghosting. The lens 10 may further comprise one or more collimators 14. The collimator 14 may be a separate layer included in the lens 10; additionally or alternately, layer 11 or layer 12 may have aspects of a collimator, and thus may function as the collimator 14; additionally or alternately, the collimator 14 may be a separate lens located between the micro-displays 2 and the reflective layer 12. The collimator 14 may be capable of concentrating rays from the micro-displays 2 in the eye box while utilizing less resolution in the periphery for an overall highest resolution and field of vision.

In one embodiment, the lens 10 may have at least three layers, including a polarized optical coating layer 12 applied to the inner surface to induce reflection and improve the contrast by eliminating stray light. This portion may contain the semi-spherical (elliptical) combiner. The middle layer may include polarization to create a perceived black. The outer layer 12 may include the dynamic opacity, which may be a pixelated layer controllable by software which induces a shadowing over the same area as the reflected augmented reality image for enhanced viewing even in bright light settings.

In the lens 10, two special cases of wave interference may be accounted for. In the focal point, rays from a point light source may meet again and may constructively or destructively interfere with each other. Within a small region near this point, incoming light may be approximated by plane waves, which may inherit their direction from the rays. The optical path length from the light source may be used to compute this phase. The derivative of the position of the ray in the focal region on the source position may be used to obtain the width of the ray, and from that amplitude of the plane wave. The result is the spread function, whose Fourier Transform forms the optical lens design.

In the optical engine, the inside portion of the lens holding a portion of the collimator, in the form of an optical oval (ellipse) which is akin to a plano-concave lens, which has a negative focal length and is typically used to diverge collimated beams of light in instruments like Galilean-type beam expanders or telescopes, or in this case to collect the light and focus it into the eye-box. The spherical aberration introduced into the wavefront by a plano-concave lens is negative, and as a result, the lens can be used to balance the positive spherical aberration introduced by positive focal length singlets.

The optical engine of the system may use an ellipsoidal reflector in the optical combiner reflective lens placing a display, so that there is a high pupil count and maximum clarity and focus to the eye.

The AXR surgical system may further comprise one or more microphones in communication with the central processing unit, where the system is capable of being controlled via voice input via the microphone, input from the eye-tracking subsystem, or a combination of voice input via the microphone and input from the eye-tracking subsystem. The one or more microphones may be configured to create noise cancellation, or the AXR headset may include noise cancelling microphones to reduce, eliminate, or remove background noise so that the receiving person, device, or AXR headset itself can better understand the speech of the user. The wearable device may further comprise a battery and a remote communication device such that the wearable device is wireless and has communication features. The AXR headset may contain one or more batteries. In the case of more than one battery, the primary battery may be located in an external position on the headset in a manner to facilitate removal and replacement of the battery during use. The primary battery may include a mechanism for a spring-loaded battery to facilitate removal during use. In case of primary battery exhaustion, a surgery tech may press the spring-loaded battery in the back of the headset, then reattach a new, fully charged battery. The AXR headset in this instance may include a hot-swap feature, which may include one or more secondary, typically smaller, batteries, which typically would only carry enough capacity to last a few minutes. Thus, when the primary battery is exhausted, the common battery control circuit may shift to the auxiliary battery to keep the headset functioning with all features continuing until the primary battery is replaced. The system may include a battery full/battery empty capacity feature which alerts the user and others that there is only a certain about of battery charge remaining so that a timely battery change may be planned.

Figure 16:
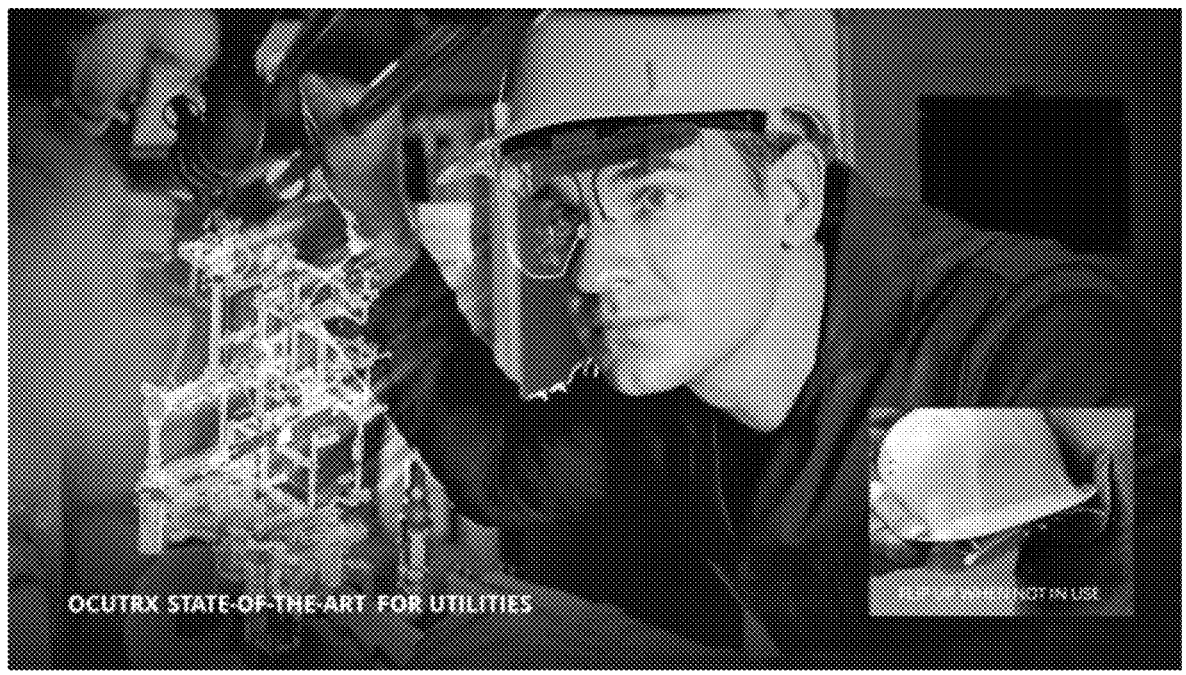
FIG. 16 is a perspective view of the AXR surgical system headset with a visor-type design.
Figure 17:
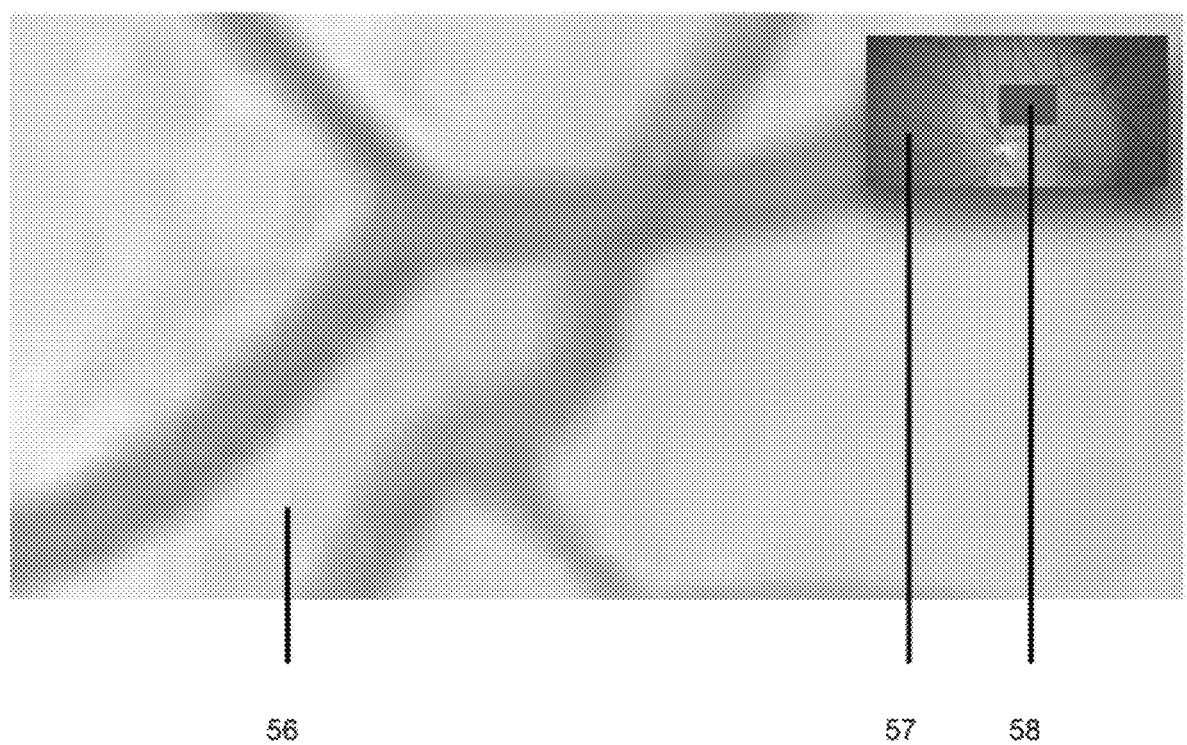
FIG. 17 is a diagrammatic view of the picture-in-picture portion of the virtual overlay software and hardware, showing a surgeon at full magnification a smaller picture of the entire FOV for better orientation.

In one embodiment, the AXR Headset 1 may have a visor design, which may be open and provide both peripheral and downward viewing beyond the lens. The system may include a clip-on corrective lens that is capable of being clipped on at the open potion of the bottom of the lens so that users with presbyopia can have their own prescription attached to the lens, such that when viewing surgery tools or other items, their own prescription is included in the view. The visor may even be cantilevered over the head, or away from the head, if necessary, in emergency situations or off surgery times, in order to provide the surgeon with an opportunity to still wear the wearable device 1, but have the visor be out of view, as shown in FIG. 16.

The Wireless Technology Subsystem.

The wearable device 1 may be lightweight and may be wireless. One of the ways to reduce weight is to have only the cameras, a battery, and sensors in the headset 1 with connectors to a WI Gig modem using the fastest wireless protocol available, such as the IEEE 802.(a,y) protocol. Another embodiment places the intelligence in the headset 1, such as a Qualcomm XR-2 chipset, and have the chipset circuit board be connected to WI Gig modems to send/receive streaming video to/from another WI Gig connected location, such as a digital microscope, endoscope, or other surgery imaging device. In the case where the AXR headset receives video feed from such a surgery system, either a wire or wireless connection can be made.

While WIFI IEEE 802.11 may work, the best method would be to use a WI Gig 802.11(ad;ay, ax) so that uncompressed video can be sent from any image producing system to the AXR headset. In addition, the AXR headset may include a 5G modem to be capable of edge computing at super-fast speeds. Edge Computing is a technique to bring data back from the cloud to a localized network where all computing goes to an on-site or close-by data center. The wireless software may leverage existing wired/wireless networking infrastructure to achieve interactive low-latency peer-to-peer connections. Latency is a time interval between the input to a simulation and the visual or auditory response to this input.

The software may runs as a two-way communication between a host/server and a client to transfer data, images, and telemetry information between the two. The client software may handle remote inputs, which are sent back to the server and evaluated or executed. This may enable high-performance computing to be processed by a powerful machine remotely through the cloud or on the same network. This methodology may work on wired, wireless, and cellular networks such as 5G. Multiple clients can connect to one host to enable a multi-user interactive broadcast experience, such as in a teacher classroom situation. The client may connect to the host and send controller data to the host while simultaneously receiving bitstream audio/video output from the host.

The software may enable cross-platform clients to efficiently render the incoming frames using a variety of coding libraries, such as OpenGL or Metal. The client may support Windows, macOS, x86-64 Linux, Android, iOS, and chromeOS and can be adapted to work with future operating systems. The software currently supports up to 4k at 120 frames per second, but a future version could have increased resolution and frame rates. Frame rate is expressed in frames per second (FPS) which is the frequency rate at which consecutive images called frames appear on a display. Increasing the frame rate of video divides this sequence of images into smaller periods of time, which is another method to reduce the latency and improve system performance, which is beneficial in a surgery visualization situation.

Wireless communication may also be accomplished through optical communication or through radio-frequency (RF). RF requires a transmitter and a receiver or a transceiver that incorporates both. RF communications may be used over a proprietary or a defined protocol such as Zigbee, Bluetooth, Bluetooth Low Energy, Z-wave, or Wi-Fi. A transmitter module is an electronic sub-assembly that is capable of transmitting a radio wave and modulating that wave to carry data. A receiver module is also an electronic sub-assembly that receives a modulated RF signal and demodulated it.

The wireless technology may also employ video over IP, also called streaming, using existing standards or proprietary methods for encoding the material into a bitstream, and then using an internet protocol (IP) network to carry that bitstream encapsulated in a stream of IP packets. A bitstream is a sequence of bits. A bit is a basic unit of information in computing. A bit represents a logical state of two possible values, which are most commonly represented as a "1" or "0" or binary digit. Because of the sequential nature of the video signal, resending packets is not an option. Additional error correction information may be added to the data transmission to ensure the stream can be reconstructed even if a few packets are lost in the transfer. The surgeon may additionally or alternately wirelessly receive a 3D video feed from a digital microscope with wireless output, into the AXR headset, providing the surgeon with an alternative surgical video input.

The system may utilize a high-resolution high-speed wireless video connection from the 3D digital microscope to the AXR headset's antennae FIG. 3, or from external sources, like being connected together with a 5G Multi-Access Control (MEC) system which has antennas located within a surgery suite or hospital or clinic with the database also inside the perimeter of the building. The 5G MEC connected to the ADMO3DV surgery system in combination with the wireless system of this invention connected between DOS3DV to the AXR headset provides crucial speed of download and uploads, critical in surgical life-threatening situations.

In this instance, since the 5G MEC is a closed system which does not permit the computing and analysis end of the transfer chain to go "outside" of the internally controlled system (surgery suite or hospital walls), thus it can provide throughput rates with as little as 10 millisecond delays. This is compared to a typical wireless internet or cell system which may have 60-90 or more millisecond or up to a minute delays and would typically have trouble with reliable downloads of compressed imagery. In this fashion, on any of the viewing options of the ADMO3DV system, when a surgeon needs to see a pre-operative 3D MM or CT scan which was not already loaded into the ADMO3DV System FIG. 16 the same can be presented for viewing in the most rapid method available. Internally, the ADMO3DV system has a "gateway" in a combination of hardware and software so that both wired and wireless views are shown in with approximately the same latency as an actual wired HDMI system and may be synced with one or both of the wired visualization options (the autostereoscopic 3D monitor or DOS3DV) or together with one or more wireless headsets and one or more wired display systems to present a simultaneous view on all the wireless headset(s) and wired display systems from the original camera(s) source.

The Eye-Tracking Subsystem.

The eye-tracking subsystem of the AXR headset 4 may work through hardware and software. The software may be connected to the system's GPU working in connection with the system's modular controller. The eye-tracking may be captured by infrared light being projected into the user's eye, which may create a glint or reflection, which may then be captured by one or more IR sensitive cameras 8. The eye-tracking subsystem 4 may be capable of capturing the glint from the eye from 30 frames per second to 500 frames per second. This information may be stored in real-time in the CPU and DSP, and then processed into a virtual space represented by x,y,z or Cartesian coordinates. These coordinates may provide the system with the information about where the user's gaze is in relation to the reflective lens and the alpha matte layer so that both stay aligned with the user's gaze. The eye-tracking subsystem may be used to map the user's eye gaze and adjust not only the reflected images or video but also the alpha matte image located on the separate plane to keep the alpha combined image aligned with the eye box. Thus, the eye-gaze and the alpha matte layer may be controlled by the eye-tracking subsystem 4 to always stay in sync.

In addition, eye-tracking may be used as an operator command option, where an operator would look or gaze at a virtual menu projected in 3D viewports and be able to select one or more options by staring or blinking one's eye while gazing at the menu.

Further, the eye-tracking subsystem may also be used to keep the pixels in the autostereoscopic 3D monitor always aligned with the user.

The all-Digital Multi-Option 3D Viewing Theatre.

The ADMO3DV system may be a non-invasive robotic arm system with a large electronic actuator lift in the form of a cylinder mounted on a smart pedestal on which is hung a translating top to hold a balanced cobotic arm system. The system may have a cabinet and drawer system, described herein, and may contain the main computer, control, and wired and wireless connection/transmission system. The system may have its own keyboard and monitor for inputting settings, connecting with other OR equipment, and inputting or outputting EMR an imaging. The non-transitory model view controller (MVC) may synchronize the subsystems and controls all input and output according to the software programs. It may also house and control all the subsystems, including the AXR headset and cobotic arms with their viewing options as well as the DCS3DM microscope. An operator may input the appropriate settings and model the control system may utilize keyboard, Bluetooth, voice control, eye-tracking, or gesture recognition or other technologies identified herein, and may also utilize SLAM and 6DoF technologies to operate properly wirelessly or use any other sensing and control technique stated above. Alternatively, one or more of these technologies may be used together in order to access and manipulate a control of the viewing system or microscope system attached to the cobotic arms. This method may allow the user to control the AXR system, autostereoscopic 3D monitor, DOS3DV, 3D microscope, or other external equipment or systems via wired or wireless connection without requiring input through foot pedals, buttons, hand dials, or other hardwired methods of control.

Combining two or more methods of control, i.e., voice with eye-tracking, may provide redundancy and ensure proper operation of controls.

The ASMO3DV system may provide an enhancement to existing surgery systems in several ways. First, as time is money, a surgery team does not have to re-position the typical 3D television monitor as the cobotic arms move the monitor to the exact position needed by the OR healthcare provider, based on the sensing and control technologies outlines herein.

The 3D Autostereoscopic Monitor Technology.

In the preferred embodiment, the monitor, which may be mounted on a cobotic arm, may be at least an 8K resolution display with interactive 3D video images, which appear through the use of a lenticular lens or parallax barrier over an LCD, OLED, or any other emissive display technology. With an 8K image, a video feed split into right and left eye images may still able to present a full 4K resolution to each eye. The 3d perspective source image may be brought into the system from, for example, two 4k or greater image sensors. The source images may have an angular deviation to represent the natural displacement of human eyes in order to create an apparent 3D view.

The optical system of the autostereoscopic display may direct the pixels of the corresponding left or right image subcomponents of the 3D view to the correct eye of the user. For the user to accurately view 3D images on the autostereoscopic monitor, the source for the display must accommodate for the lenticular lenses or parallax barrier. To accommodate for the display technology, a source image must be processed via a shader, or computer algorithm, to accurately place the pixels on the display technology behind the specific optical system elements in order to present to each eye the information that allows the user to perceive 3D and depth information.

A shader is a type of computer program originally used for shading in 3D scenes (the production of appropriate levels of light, darkness, and color in a rendered image). They now perform a variety of specialized functions in various fields within the category of computer graphics special effects unrelated to shading, for example pixel placement as described above to utilize the correctly correlated optics presenting to the user's binary view. Traditional shaders calculate rendering effects on graphics hardware with a high degree of flexibility. Most shaders are coded for (and run on) a graphics processing unit (GPU), though this is not a strict requirement.

Shading languages are often used to program the GPU's rendering pipeline; with shaders, customized effects can be used. The position and color (hue, saturation, brightness, and contrast) of all pixels, vertices, and/or textures used to construct a final rendered image can be altered using algorithms defined in a shader, and can be modified by external variables or textures introduced by the computer program calling the shader.

The Digital Ocular Technology.

The DOS3DV digital ocular may consist of two ocular viewports existing in a housing mounted on a cobotic arm. The operator may put his or her eyes up to the eyepiece affixed to the housing and can see the wired or wireless surgery video feed in 3D stereoscopic vision emanating from the digital microscope through an optical engine, described below, which may end in a mirror that projects the 2D image to each eye stereoscopic offset to form a 3D image.

The cobotic arm may move to, away, and with the operators with one or more of the described sensing and control technologies, including facial recognition, eye-tracking, head-tracking, and SLAM sensors. With these sensors mounted in the DOS3DV housing, it can identify an operator of first origin, or one who has been programmed into the system. The DOS3DV can move from a position of pre-programmed repose to "active" state where the sensors find the operators face and eyes and travel to the operator stopping at a safe zone 16 mm from the eyes. If the operator moves his head or posture, the cobotic arm may continue to adjust through the sensing technology to move and adjust with the operator.

The DOS3DV may use the same basic optical engine technology as in FIG. 7 for presenting a view to the operator as in the AXR Headset Figure except that instead of a conic combiner 46 (at the last of the optical chain) and replace that lens with a full mirror. The converted optical engine may be housed in a casing head with eyepieces. The casing head may contain interpupillary adjustment, which may be on a worm drive and may be adjusted via Bluetooth just like the AXR headset IPD.

Smart Pedestal Technology.

The ADMO3DV may be self-moving from one position to another pre-programmed position by using virtual track markers on the floor (RFID, IR, or Optical) to accomplish its retreat from the gurney after surgery. Or if the OR team desires, it can spin 180 degrees at an out-of-the-way point and then use the fiducial markers to return to a target on the opposite side of the bed. In this fashion, the ADMO3DV can reposition itself from one side of the bed to the other. Targeting markers (on the floor) are based on optical pattern recognition technology, infrared technology, or RFID technology, which may require almost zero maintenance, provide millimeter accuracy, and take less than minutes to complete. Further, LiDAR or ultrasonic proximity sensors mounted on the system can automatically stop the unit if a person or item is in the way. In this fashion, the entire system can be programmed move into active position alongside of a surgery gurney, guided by one or more of the sensing and control techniques mentioned herein, or the ADMO3DV can automatically re-position itself to to a different location for a different type of surgery or any other pre-programmed location at the command of an operator. This may result in reduced time and physical effort in the OR in transitioning from one patient to the next. It is especially helpful in the instance of a slate of cataract surgeries, so that it can move from one side of the gurney to the other automatically depending on the eye that is undergoing surgery. As it is now, if a surgery lasting 7 to 10 minutes is performed on a right eye, it may take as much as another 10 minutes to reposition the monitor after surgery if the next surgery is on the opposite eye. Further, a surgeon currently with major manufacturer's technologies has to have manually measured from his chest to the monitor the exact positioning differential to see a 4k monitor. The ADMO3DV system may automatically move. Second, having the image in glasses worn by the surgeon is highly preferable to having to look across a patient to see a television monitor. Third, with the voice plus eye-tracking extent in the system, a surgeon is untethered from most foot pedals, hand dials, or other hardwired methods of controlling the surgery. In addition, the constant movement from a large field of vision to see the existing television screen back to near focus in a digital microscope or to hands to confirm acquisition of a tool can tax a surgeon after long surgeries or multiple surgeries in a row. With the voice plus eye-tracking of the present system and the image right in the surgeon's eyes, this issue is resolved, providing the surgeon with maximum comfort during surgeries and the least taxing method to the surgeon's eyes.

The Digital Camera Sensor 3D Microscope.

Figure 10:
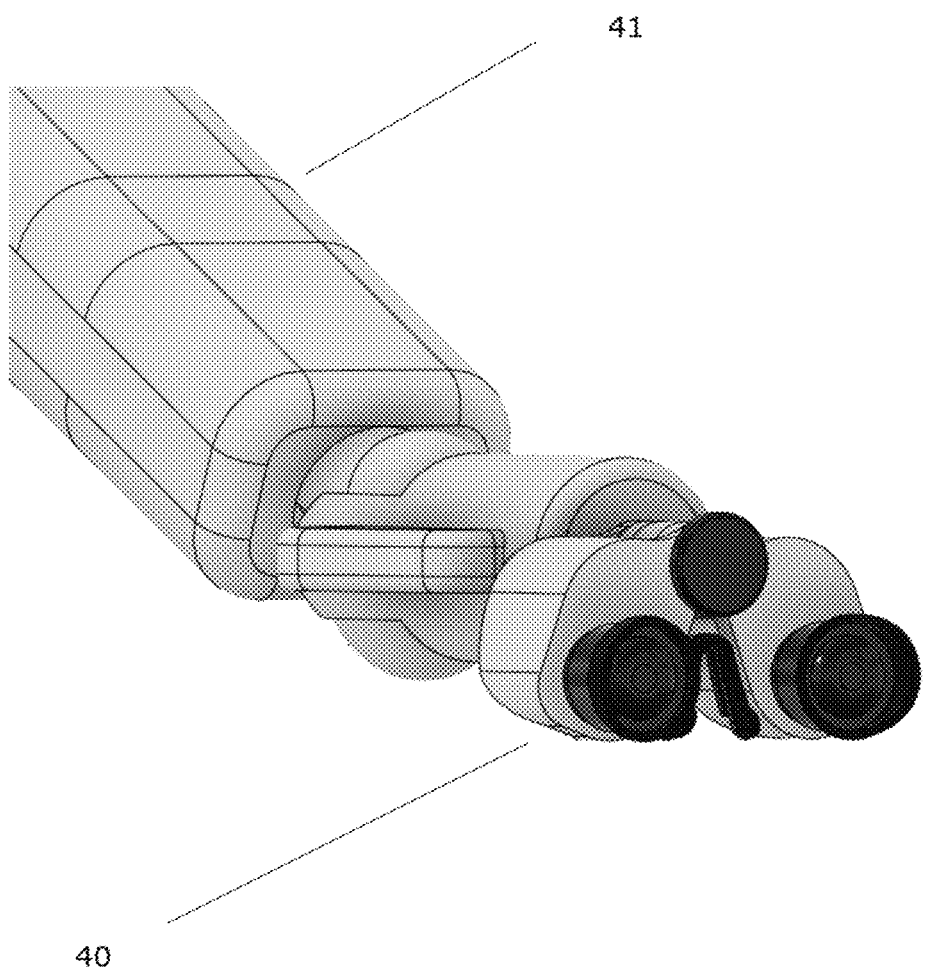
FIG. 10 is a view of the DOS3DV mounted on a cobotic arm.
Figure 11:
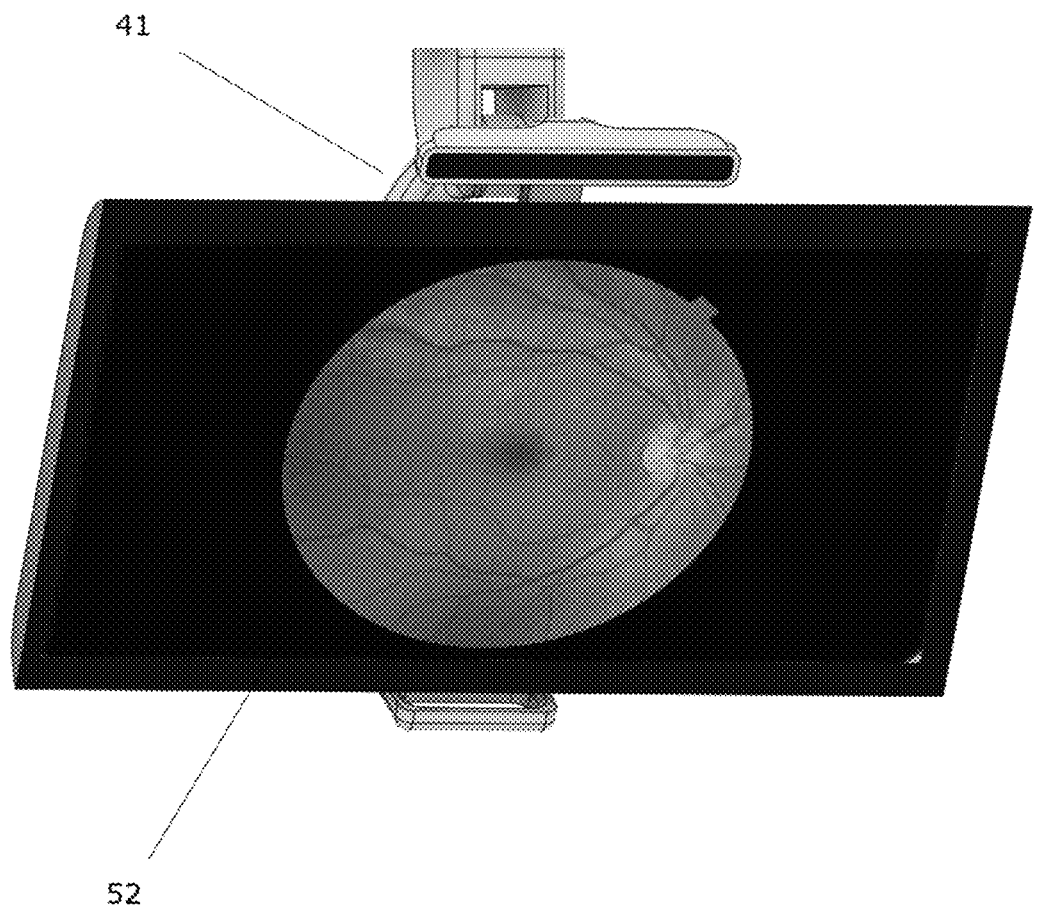
FIG. 11 is a view of the autostereoscopic 3D 'glasses free' monitor on the system.

As shown in FIG. 10, the one or more cameras 5 may alternately be housed within their own system 40, like the DCS3DM system, and may be connected wired or wirelessly to the AXR headset 1. The DCS3DM system 40 may consist of two parallax mounted cameras 5 with optical zoom to create a 3D viewing experience and may be mounted on a six-axis robotic/cobotic arm 41 for surgery use, as shown in FIG. 11. The DCS3DM may then send video over any of the methods listed in this application to the endpoint viewports.

Most major surgical device manufacturers begin with legacy equipment and then add a digital component. This means typically they are less ergonomic, less dynamic, less functional, and are based on older camera/display technology. However, the ADMO3DV system may be all digital and may only employ ocular lenses to make the digital images.

The ADMO3DV may use cinematic full-frame camera sensors with large pixels of over 6 microns. For ophthalmic surgeries, light inside the retina needed for surgery with 'normal' sensors must be very bright; however, by utilizing camera sensors with very large pixels, the light may be greatly reduced so that the retinal light toxicity is dramatically reduced.

By using these specialized sensors, which requires a different and unique placement, housing, and software, the color spectrum can be increased from 1 billion potential colors to over 69 billion potential colors. This means that the cameras can see colors that the human eye cannot so that the software and algorithms can be programmed to identify a particular color spectrum and that would be all cancer cells. Or the color spectrum could be all retinal membrane tears, which need to be removed. In this fashion, once all the pixels that correspond to a particular color spectrum (and the corresponding cells which make up that spectrum) can be highlighted for a surgeon, ensuring that the surgeon gets all of that identified spectrum of cells.

At high magnification (6× to 12×) the AR headset may continually provide orientation when at high magnification levels so the surgeon is always oriented to the unmagnified view.

The Cobotic Arms.

The six-axis arms cobotic arms may be either gear and axis based articulating robotics or can be based on scara robotics. These robotic arms may combine robotic automated movement combined with the collaboration of an operator, who may activate and control the cobotic arm 41 by voice control, eye-tracking, gesture recognition, haptic technologies, touch, or other control technologies mentioned herein or with a joy-stick. Alternatively, two or more of these controls may work in combination with another for control.

The cobotic arm 41, when voice or otherwise activated using the technologies described herein, may recognize the exact site of the surgery on a patient's body to be viewed during the surgery from pre-programmed information and may travel according to the software and the ability of the six-axis arm 41 to the exact position the camera is needed for surgery. The six-axis arm 41 may be connected to a stationary or movable side-carte component stationed on the floor or connected to a boom on the ceiling or a wall.

The arms 41 may be powered by motors and may be gravity-compensated and may respond to either the touch of an assistant, or by voice command, or any other of the control technologies mentioned herein. The cobotic arms may combine axis of the scara type robotics with the six-axis gear articulating arms for the best method of gross movement combined with fine movement.

The cobotic arm 41 may receive and transmit for instruction and feedback/tracking either sound, light, vision, movement, and/or sensitive sense-of-touch (force tactile transmission) to a remotely located user or controller in real time. The precision motors contained within the cobotic arm 41 may use the haptic sensors or internal algorithms to work with a user's so that, for instance, a slight touch in the direction of its repose may cause the cobotic arm 41 to continue to its position of repose. Likewise, if the arm 41 in in a position of repost, a slight push towards another programmed or learned location will cause it to activate the motors to continue to that location. The cobotic arm 41 may also be manually placed in a certain position by a user, and the cobotic arm's controller may remember the exact movement so that it can duplicate that movement automatically upon command by any of the technologies mentioned herein. For instance, if a cobotic arm 41 is manually placed at a surgery location needed for viewing the surgery site, and then, during the surgery the patient developed a bleed or other cause of emergency, the cobotic arm 41 could be activated to move to its repose position. Once the issue was resolved, the cobotic arm 41 with the camera may, on command, return to the exact location needed to continue the surgery. Also, a surgeon or tech may slightly push the robotic arm 41 in one direction, and the cobotic arm 41 would continue to move to that direction until it ended up in the intended position. Likewise, if a surgeon or assistant pulled on an arm 41, it would continue until it reached a predestined spot.

The Multiple Overlay Visual System and Sensors.

Figure 13:
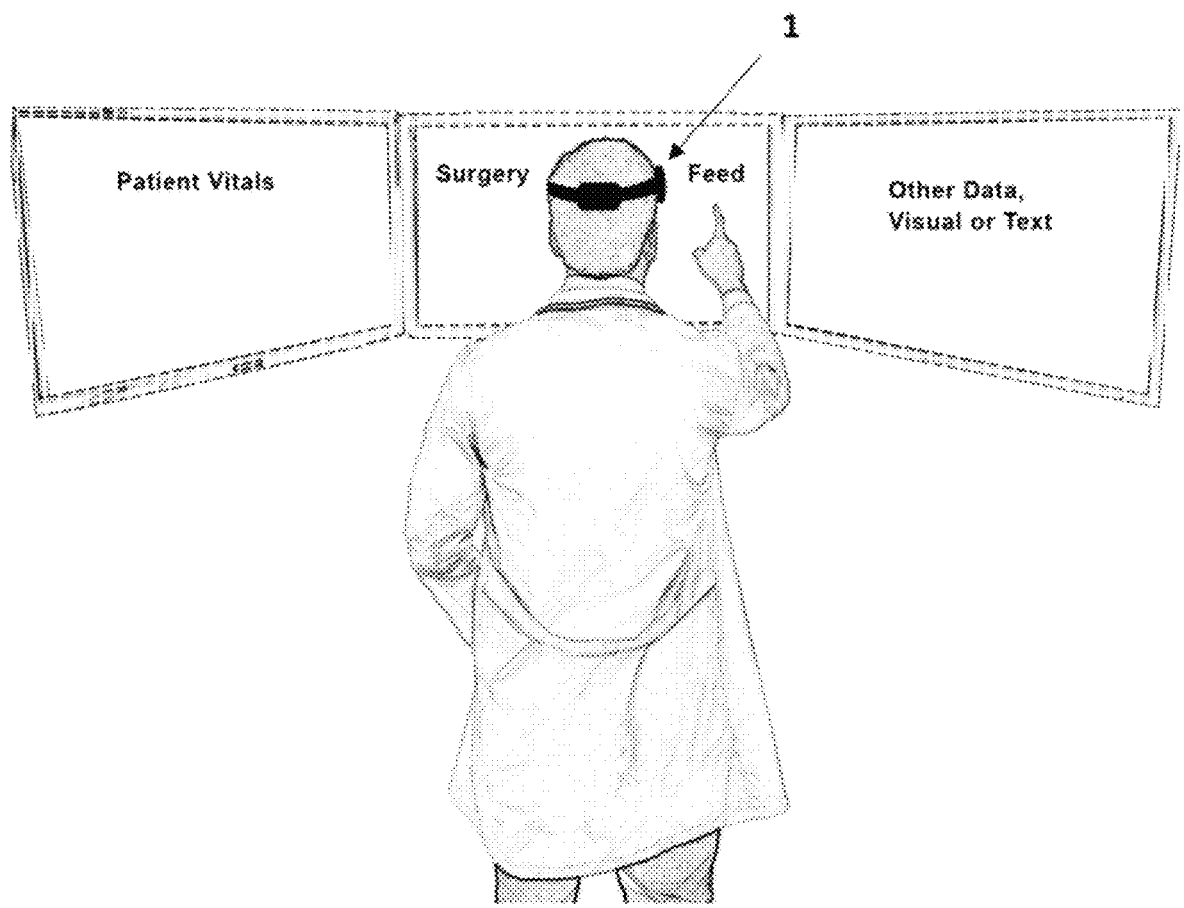
FIG. 13 is a back view of a person wearing the AXR headset, illustrating different views presented by the virtual overlay.
Figure 14:
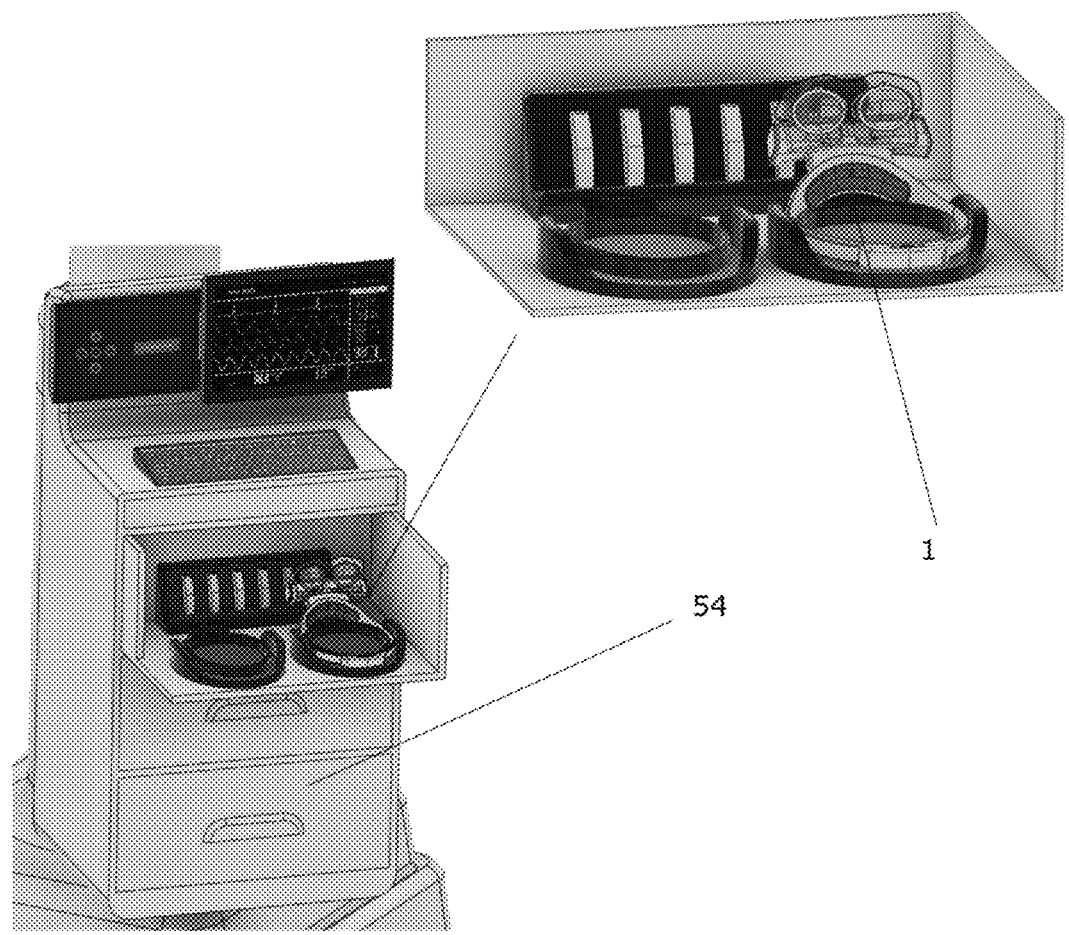
FIG. 14 is a perspective view of the charging cabinet housing the control system and computer and depicting the AXR headsets being charged and uploaded with surgery imaging data and EMR information.
Figure 15:
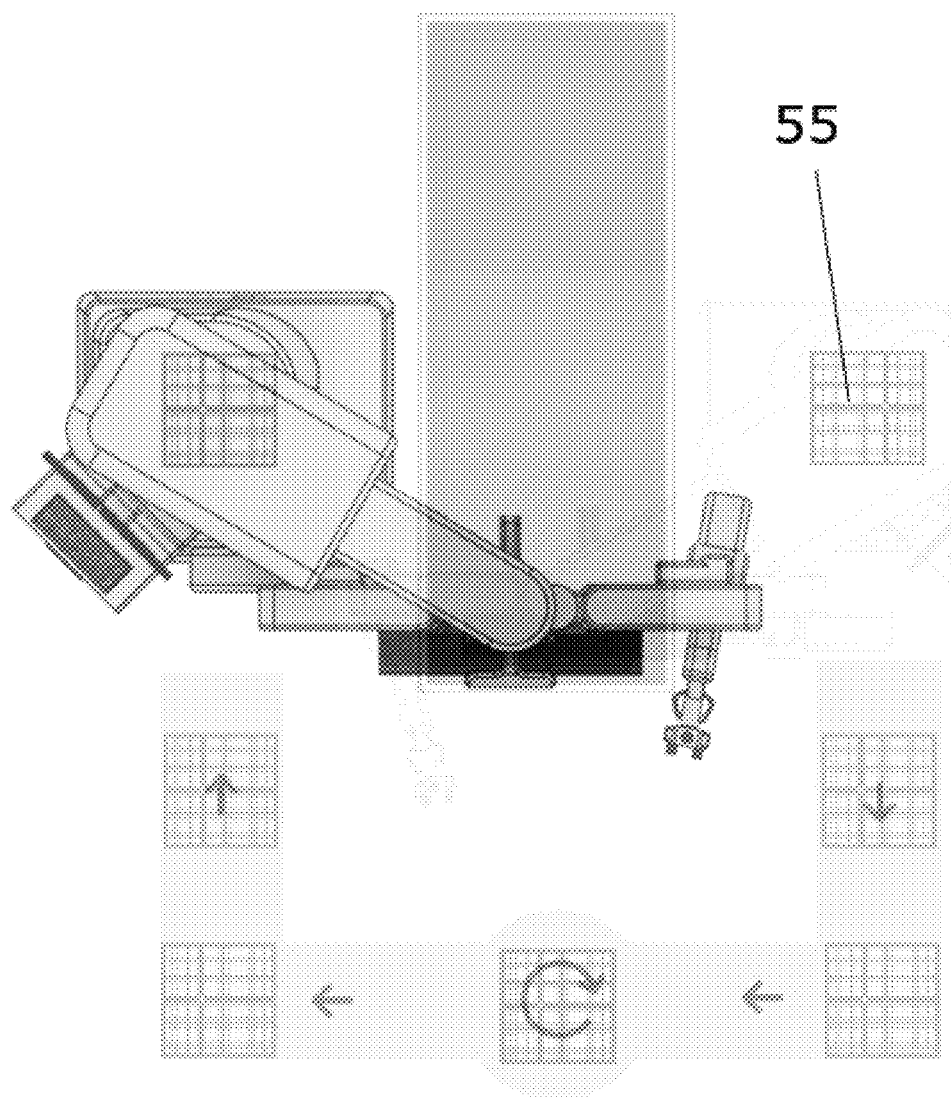
FIG. 15 is a perspective view of the smart pedestal of the surgery system showing its automatic change of position upon command.

The ADMO3DV system or AXR headset may be capable of overlaying information, such as text and graphs, in a virtual display over the operating view, as shown in FIG. 13. the system may allow the surgeon or user to control and present the overlayed information, pictures, graphs, or videos in other views inside the headset via a visual presentation subsystem. The visual presentation subsystem, powered by IMU, SLAM, and/or eye-tracking technologies, may provide an overlay of vital information, such as text and graphs, in virtual display over the 3D operating view. The visual presentations may be like windows or chyron generated view visible within the AXR FOV and may be virtually presented in a certain pre-set location of the user's view. For example, for an ophthalmologic surgery, the system may display intraocular pressure, cut rate, and flow rate or may show which mode a surgeon is in, such as vitrectomy, extrusion, dense tissue, etc., and may retrieve and track a preloaded surgery plan. For other surgeries, such as vascular, ENT, thoracic/cardiac, or orthopedic, this information displayed may vary depending on the equipment or information useful to the surgeon during the surgery.

Alternatively, the overlay may be used to view preoperative or interoperative images in virtual format, including pictures, videos, MRI's, CT scans, and the like. This information may be visible upon voice command of the surgeon, and the system may provide the user the option of displaying information at the bottom, side, or top of the AXR lens view. In other words, for example, if using eye-tracking or head tracking, the surgeon may move his or her head or eyes at a predetermined degree of rotation, for instance 15 or 30 degrees either to the side or up and down. With this turn of the eyes or head, the surgery video feed images may disappear and alternative information like patient vitals may appear. When the surgeon moved his or her head or eyes the opposite way, equipment readouts, preoperative information, or other important information may appear. Likewise, when the surgeon moves his or her head or eyes back, the surgery images may appear to return focus to the surgery. When the surgeon looks a certain pre-set degree downward, the surgery images may disappear, and the surgeon could refocus on the RR patient and surgery. Alternately, the system can be set to leave the information always in view. Thus, a surgeon who does not like distractions can have the option of making a slight head or eye adjustment as needed to see the information. For example, while a retina surgeon is in laser mode, he or she may enable the information display to show power, standby versus on, duration, and intensity.

The system may also provide for intraoperative optical coherence tomography (iOCT). While typically there is a need for a technician to also be in the room to assist with the iOCT's operation, the system may replace the technician with its voice plus eye-tracking commands.

Optionally, the AXR headset may use IMU, SLAM, eye-tracking, and/or other technology to permit the surgeon to move his or her head forward or use an eye movement or other manner of control described herein to cause the z coordinate to reorient to magnify or reduce the surgery image.

For the system to provide these options, the AXR headset 1 may be embedded with SLAM, 6DOF, inertial measurement units (IMU), or eye-tracking technology, which may interpret the angle of the user's head or eyes versus the displayed image. Then, when either the eyes or head move to focus on a portion of the image that is originally on the edge of the view, the system may digitally reposition the image to the center of the user's visual field, providing a high-focus view independent of where the image was originally located.

The head tracking subsystem 3 may include an internal array of IMUs 7, which may include one or more accelerometers, gyros, and/or magnetometers. Using these sensors, the system may be capable of automatically enabling and switching between camera systems depending on the position of the surgeon's head. For example, when the surgeon looks down, the system may enable the front-facing cameras 5, and then when the surgeon looks up or straight ahead, the system may enable the downward cameras 5 to permit the surgeon to comfortably find a forward-looking position while the downward facing cameras 5 capture the surgeon's hands and the operating space. Upon a voice command issued from the surgeon, the system may switch off the RR cameras 5 and convert to projecting the images from a scope or digital microscope.

The accurate alignment of AXR images with RR images may be achieved by using AI and a set of trackers 6, which may be used to determine the exact position of the cameras 5 and the patient's body. The AI engine together trackers 6 may identify and track fiducial markers placed on the surface of specific structures that remain still during surgery, such as iliac crest, clavicles, etc., and thus provide the system with points of reference. The system may take the fiducial marker information and fuse it with other inertial measurement data, which may be provided by the internal array of inertial measurement units 7, to provide a stable localization of the overlay system. The system may utilize proprietary 2D/3D software maximized for surgery.

The system may include a six degrees of freedom (6DoF) sub-system capable of providing real-time interfacing and no time loss between accessing 3D-type CT or MRI scans and projecting those images for surgery. The 6DoF subsystem may allow the system to pin 2D and 3D images to a virtual marker in virtual space. The 6DoF sub-system may comprise a high-performance tracking system driven by multiple sensors and cameras, including a ToF camera and high camera-frame-updating-rate (>90 fps) and global shutter features. This may keep SLAM tracking positions and 3D virtual images in the right place at all times, with little to no drift. This may ensure, in a surgery application, that a virtual MRI of a heart stays locked in place when the surgeon looks for other views, or when looking away from the surgery to speak to a technician.

The system may be capable of displaying CG images over the top of pass-through RR. This may include presenting images generated using a fusion of optical images with near-infrared fluorescence images not visible to the human eye. These images can provide more useful immediate feedback that is overlayed in context to what is needed, such as blood flow. This technique may be used to increase precision by providing additional data for the surgeon to consider. Using this technique, surgeons could be able to detect blood vessels under the organ surface or detect other tissue abnormalities.

The system may be used as a digital magnifier, providing up to 12× magnification with both near-field viewing and wide-field viewing.

As noted above, the system may be in communication with one or more second systems such that one or more remote users can view the images from the system on the one or more second systems and communicate will the user and other remote users. By utilizing gesturing recognition and other mentioned technologies embedded in all user's headsets, any number of wired or wireless connected, or networked users may see the same virtual image. Then, any connected user can point to a specific point or set of points, or define one or more areas in virtual space, on the commonly seen virtual image in all the user's AXR headsets, which may then communicate and correspond that same reference information into the view of a select set or all other user's AXR headsets or to any other monitors and displays in the network. This technique may work with either a current simultaneous view or a current or past picture or video feed. Since the controller on all connected and simultaneously viewing headsets knows exactly where each pixel exists in the displayed virtual image, it may be able to identify the specific point or set of points, or area or areas, of interest and transmit that information wirelessly, or over a wired connection, to create a corresponding marker on all connected user's headsets so that all connected users can see and understand the specific point, set of points, area, or areas of interest originated by the initial pointing user. Likewise, the point or set of points or area or areas commonly displayed may be used as a point of reference or a measurement. In addition to images, any textual, graphical, or other information may also be commonly viewed by connected users. In addition, any connected AXR headset user using the technologies mentioned herein or through AI techniques may choose to view commonly displayed 2D or 3D images or 2D or 3D models in the same perspective as another; or any user may choose a different perspective of the same 2D or 3D images or models.

Picture-in-Picture Technology.

When the user begins to zoom in or magnify an image, a picture-in-picture may appear, which may allow the user to keep their orientation and understand where they are located within the whole image, as shown in FIG. 18.

Picture-in-picture technology in the ADMO3DV system may permit a user of any of the viewports to watch two images or videos (primary and secondary) simultaneously. The primary picture 56 may fill the entire screen or projection across a lens, while the secondary picture may be a smaller (approx. ¼th of the primary picture size), floating window pinned to a corner of the screen (always on top of all other windows), which may allow users to keep an eye on what is happening in both images at one time. The primary picture may be a digital image created by the DCS3DM and viewed in any of the viewports. The DCS3DM may have the ability to magnify or zoom up to 12× with 2× optical and 6× digital magnification. The original digital signal may always be maintained the in software, as the increased magnification is may be a digitally enhanced copy of the primary picture, once the user begins to zoom, the image or video on the lens may become the primary picture, and a smaller screen may appear as the secondary picture. The centers of two related maps may indicate the same x,y,z coordinates. A secondary picture map 57 may represent the area on a smaller scale, and while the primary picture may be a digitally magnified image of the area of interest, the secondary picture may remind the operator where he is in the "big picture."

This utility is designed to simplify identifying where the viewer is in relation to the non-zoomed image. This feature may permit the user to examine the same region of the image with different zoom levels with respect to the whole image before it was magnified. Through software and the controller, each picture may be a dynamically linked map that follows along the same coordinates. Changing the coordinates of the center on one of them may lead to an automatic displacement of the center in the same point of the second and a coordinate display unit informs of the current coordinates. Thus, when a user begins to magnify or zoom in on an image or video, a secondary picture may appear on the lens of the viewport and the larger, magnified image may become the primary picture. The primary picture may be magnified as specified by the user while the secondary picture may capture the original coordinates of the primary picture before it was magnified. Through software control and menu selection, the secondary picture can be pinned to either the top left corner, top right corner, bottom left corner, or bottom right corner depending on the surgeon's preference, and can be shifted to a new location using virtual touch commands.

The secondary picture may function as a magnifying glass. In fact, there may be no image enhancing; for example, a utility for determining the coordinates uses the same data source, but not limited to the magnification of the image. The secondary picture may simultaneously capture the close-up area represented by the primary picture indicated by a 40% transparent grey shaded square called the "Magnification Identifier" that is overlaid on top of the zoomed-out image. The user may be able to identify their location in the primary picture relative to the secondary picture as it is indicated by the grey shaded square 58.

The secondary image may be a digitally altered subsampling of the primary image. Thus, the secondary image may fill the viewport showing a surgeon their region of interest, while the primary image may be placed in a corner of the viewport to serve as a map. The position of the secondary image may then be indicated on the primary image via an overlay, whether varying capacity monochrome or color. Digital altering of the primary image can include digital zooming, color contrast enhancement, color picking, or other video processing system that is useful for the surgery.

The AI and Big Data Technology.

One of the features of an all-digital system which can self-record all information and imaging is the brand-new patient and surgery data to be collected and analyzed and the introduction of artificial intelligence (AI) into the surgery headset. The surgery visualization unit may provide an unparalleled opportunity to get in on the ground floor of the data revolution where the data from surgeries can be collected and categorized in order to analyze and improve ophthalmic and other surgeries.

"Big data" refers to the interdisciplinary analysis of high volume, diverse clinical and patient information. The ADMO3DV system may house, send, and receive EMR information and imaging for surgery.

The use of such data in surgery has the potential to improve outcomes, increase safety, improve surgeon accuracy, and aid surgery planning.

The creation and analysis of vast amounts of data from the recorded video of the surgeries may integrate into a data plan at the outset of a ADMO3DV development program to alleviate some of these surgery pain points by enabling innovation, guiding regulatory pathways, and maximizing commercialization opportunities.

Big data analytics in surgery is currently in a nascent stage, however, this will not be for long. Many organizations will want to take advantage of the data collected during a surgery, especially video data which has the potential to be critically analyzed. Also, the advent of AR in the surgery room presents a new opportunity for the advanced organization to begin now to devise and combine the 3D and 4D imaging of radiologist with and AR surgeon experience.

The ADMO3DV can connect surgical quality improvement efforts with pre- and post-surgical care and linking up with quality improvement efforts in primary and nonsurgical specialty disciplines.

For instance, the ADMO3DV can take advantage of the herein described advances in computers' screens and visual perception and can record and analyze the outcomes so that this process can be one which can be repeated and learned by the surgeons and the headset. To reduce risks, the augmented reality image can show the surgeon the exact correct position of the surgical tip tool, so that risk can be reduced, and surgery outcomes enhances.

Using AI techniques embedded in the AXR headset or in a repository or neural network in communication with the one or more AXR headsets, through wired, wireless, or over 5G Edge Computing connections, one or more current or stored surgery videos or still images can be analyzed and compared against a data model or composite of data models to find either specific or general information based on specific criteria, and show a result as a virtual image(s) on one AXR headset in real-time or on a plurality of connected AXR headsets Alternatively, the AI engine may make a similar comparison with a number of specific criteria's or no criteria at all, and bring novel information inferred from the system.

Using these technologies, for instance, a 3D MRI virtual image of an organ could be managed or compared with AI by one of the techniques set out herein in virtual space by the surgeon without getting contaminated by touching a real object, in order to change the registry and orientation of the virtual organ image to match the RR organ to increase the surgeon's understanding of where to incise, inject, or perform some other similar surgical act. In the case of the manipulation of a virtual image to match a real image, as stated above, the system may increase or decrease the opacity gradient of the lenses, so that both the virtual organ and the real organ may be viewed, or aligned, by the surgeon seeing them both at the same time.

The system can be an effective tool for training and skill assessment of surgery residents, other medical staff, or students. Specialized training simulators that can interject unusual or emergency situations may be created and used to improve surgeons' skill in various scenarios, as well as to objectively measure their technical skills. The system may prove especially beneficial for trainee residents and students in developing intuition and proper decision-making abilities, which can otherwise be only gained through long clinical practice.

While the instant invention focuses on the medical applications, the same technology may be used in other sectors, where a user needs to have a primary view and the ability to have other reference views available. Further, where this invention states words like "surgeon" or "assistant" or "tech" this is used in the common context of surgery application, but the same function and features apply to anyone wearing the AXR headset.

Whereas, the devices and methods have been described in relation to the drawings and claims, it should be understood that other and further modifications, apart from those shown or suggested herein, may be made within the spirit and scope of this invention.

What is claimed is:

1. An augmented/extended reality (AXR) surgical system comprising:
   a wearable device comprising:
      one or more micro-displays;
      one or more lenses, where the micro-displays are capable of projecting images onto the lenses and where each of the lenses comprises:
         an inner layer of polarized optical coating, where the inner layer comprises a semi-spherical combiner;
         a middle layer that is polarized; and
         an outer layer, where the outer layer is a pixelated layer controllable by software which induces shadowing where the images are being projected;
      a head-tracking subsystem; and
      an eye-tracking subsystem; and
   a central processing unit in communication with and capable of controlling the micro-displays, lenses, head-tracking subsystem, and eye-tracking subsystem;
   where the system is capable of displaying images on the lenses with a position based on a user's head position as tracked by the head-tracking subsystem and the user's eye position as tracked by the eye-tracking subsystem, while allowing the user to see through the lenses where the images are not being projected.

2. The AXR surgical system of claim 1 where the micro-displays are organic light-emitting diodes.

3. The AXR surgical system of claim 1 where the micro-displays have a midrange luminance.

4. The AXR surgical system of claim 1 where the micro-displays emit at least 3,000 NITS per display.

5. The AXR surgical system of claim 1 where the micro-displays emit light of sufficient luminance that the system has an eye value of 300 to 500 NITS.

6. The AXR surgical system of claim 1 where the outer layer comprises electrically switchable suspended particle smart glass based on chiral-numatics properties of cholesteric liquid crystal and where the outer layer is not polarized.

7. The AXR surgical system of claim 1 further comprising a digital microscope, where the images are obtained from the digital microscope.

8. The AXR surgical system of claim 1 where the one or more lenses each comprise an aspheric lens.

9. The AXR surgical system of claim 1 where the lenses are capable of keystoning software distortion correction.

10. The AXR surgical system of claim 1 further comprising a six-degrees-of-freedom subsystem capable of pinning the images to a virtual marker in virtual space.

11. The AXR surgical system of claim 10 where the six-degrees-of-freedom subsystem comprises a high performance tracking system driven by multiple sensors and cameras.

12. The AXR surgical system of claim 1 where the wearable device has a visor design such that the one or more lenses provide both peripheral and downward viewing beyond the lens.

13. The AXR surgical system of claim 12 where the one or more lenses are capable of being folded over or away from a user's head.

* * * * *